US008890937B2

(12) United States Patent
Skubic et al.

(10) Patent No.: US 8,890,937 B2
(45) Date of Patent: Nov. 18, 2014

(54) ANONYMIZED VIDEO ANALYSIS METHODS AND SYSTEMS

(75) Inventors: Marjorie Skubic, Columbia, MO (US); James M. Keller, Columbia, MO (US); Fang Wang, Columbia, MO (US); Derek T. Anderson, Columbia, MO (US); Erik Edward Stone, Fulton, MO (US); Robert H. Luke, III, Columbia, MO (US); Tanvi Banerjee, Columbia, MO (US); Marilyn J. Rantz, Rocheport, MO (US)

(73) Assignee: The Curators of the University of Missouri, Columbia, MO (US)

( * ) Notice: Subject to any disclaimer, the term of this patent is extended or adjusted under 35 U.S.C. 154(b) by 862 days.

(21) Appl. No.: 12/791,496

(22) Filed: Jun. 1, 2010

(65) Prior Publication Data

US 2010/0328436 A1   Dec. 30, 2010

Related U.S. Application Data

(60) Provisional application No. 61/217,623, filed on Jun. 1, 2009.

(51) Int. Cl.
  *H04N 15/00*   (2006.01)
  *H04N 9/47*    (2006.01)
  (Continued)

(52) U.S. Cl.
  CPC ............. *G06F 19/345* (2013.01); *A61B 5/002* (2013.01); *A61B 2560/0242* (2013.01);
  (Continued)

(58) Field of Classification Search
  CPC ............ G06T 17/00; G06T 2207/30196; G06T 2207/10021; G06T 7/004; G06T 2207/20081; G06T 2207/20144; A61B 5/002; G06F 3/011; G06F 19/3418; G06F 19/345; G06K 9/00375; G06K 9/00369
  USPC ................. 348/47, 77, 135, 143; 340/573.1; 382/103
  See application file for complete search history.

(56) References Cited

U.S. PATENT DOCUMENTS 6,915,008 B2 * 7/2005 Barman et al. ............... 382/154
7,420,472 B2  9/2008 Tran
(Continued)

OTHER PUBLICATIONS

Title: "Gait Initiation in Community-Dwelling Adults With Parkinson Disease: Comparison With Older and Younger Adults Without the Disease" Authors: Matthew Martin, Mindi Shinberg, Maggie Kuchibhatla, Laurie Ray, James J Carollo and Margaret L Schenkman Date: Jun. 2002.*
(Continued)

*Primary Examiner* — Andy Rao
*Assistant Examiner* — Jared Walker
(74) *Attorney, Agent, or Firm* — Polsinelli PC

(57) ABSTRACT

Methods and systems for anonymized video analysis are described. In one embodiment, a first silhouette image of a person in a living unit may be accessed. The first silhouette image may be based on a first video signal recorded by a first video camera. A second silhouette image of the person in the living unit may be accessed. The second silhouette image may be of a different view of the person than the first silhouette image. The second silhouette image may be based on a second video signal recorded by a second video camera. A three-dimensional model of the person in voxel space may be generated based on the first silhouette image, the second silhouette image, and viewing conditions of the first video camera and the second video camera. In some embodiments, information on falls, gait parameters, and other movements of the person living unit are determined. Additional methods and systems are disclosed.

20 Claims, 27 Drawing Sheets

(51) Int. Cl.
*A61B 5/00* (2006.01)
*G08B 21/04* (2006.01)
*A61B 5/0205* (2006.01)
*A61B 5/11* (2006.01)
*A61B 5/021* (2006.01)
*A61B 5/08* (2006.01)
*G06F 19/00* (2011.01)
*A61B 5/024* (2006.01)

(52) U.S. Cl.
CPC ......... *G08B 21/0423* (2013.01); *A61B 5/0205* (2013.01); *A61B 5/021* (2013.01); *A61B 5/7264* (2013.01); *A61B 5/0816* (2013.01); *A61B 5/1113* (2013.01); *A61B 5/1118* (2013.01); *G06F 19/3487* (2013.01); *A61B 2503/08* (2013.01); *A61B 5/024* (2013.01); *A61B 2505/07* (2013.01)
USPC .............................. 348/47; 348/143; 348/159

(56) References Cited

U.S. PATENT DOCUMENTS

| | | | |
|---|---|---|---|
| 2003/0058111 A1* | 3/2003 | Lee et al. ................... | 340/573.1 |
| 2003/0085992 A1* | 5/2003 | Arpa et al. ..................... | 348/47 |
| 2004/0030531 A1 | 2/2004 | Miller et al. | |
| 2004/0119716 A1* | 6/2004 | Park et al. ..................... | 345/473 |
| 2004/0228503 A1* | 11/2004 | Cutler ........................... | 382/103 |
| 2005/0088515 A1* | 4/2005 | Geng ............................. | 348/47 |
| 2005/0094879 A1* | 5/2005 | Harville ........................ | 382/209 |
| 2007/0003146 A1* | 1/2007 | Ko et al. ........................ | 382/224 |
| 2007/0263900 A1* | 11/2007 | Medasani et al. ............. | 382/103 |
| 2009/0079559 A1* | 3/2009 | Dishongh et al. ........ | 340/539.13 |
| 2009/0089089 A1 | 4/2009 | Jang et al. | |

OTHER PUBLICATIONS

Title: "The timed get-up-and-go test revisited : Measurement of the component tasks" Authors: James C. Wall, PhD ; Churan Bell, BS ; Stewart Campbell ; Jennifer Davis Date: Jan./ Feb. 2000.*

Title: "Arbitrary Viewpoint Video Synthesis From Multiple Uncalibrated Cameras" Author: Satoshi Yaguchi Date: Feb. 2004

Title: "Three dimensiona Gesture recognition" Author: James Davis.*

Title: "Recognizing Falls from Silhouettes" Author: Derek Anderson Date: Aug. 2006.*

Harvey, N. et al, Speedup of Fuzzy Logic through Stream Processing on Graphics Processing Units, In Proceedings: IEEE Congress on Evolutionary Computation, 2008, pp. 3809-3814.

Sledge, I.J. et al, Emergent Trend Detection in Diurnal Activity, 30th Annual International IEEE EMBS Conference, Vancouver, British Columbia, Canada, Aug. 20-24, 2008, pp. 3815-3818.

* cited by examiner

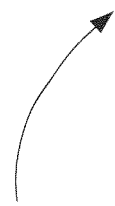

| Rule | | On the ground | Time duration | Change in speed | Motion | Oscillating | | Fall |
|---|---|---|---|---|---|---|---|---|
| 1 | If | High | Long | | | | Then | High |
| 2 | If | High | Moderate | High | | | Then | High |
| 3 | If | High | Moderate | | High | | Then | High |
| 4 | If | High | Moderate | | Low | | Then | High |
| 5 | If | High | Moderate | | | | Then | High |
| 6 | If | High | Short | High | | High | Then | High |
| 7 | If | High | Short | | | High | Then | Medium |
| 8 | If | High | Short | | | Medium | Then | Medium |
| 9 | If | Medium | Moderate | High | | | Then | Medium |
| 10 | If | Medium | Moderate | High | Low | | Then | High |
| 11 | If | Medium | Short | | Low | | Then | High |
| 12 | If | Medium | Short | | | High | Then | Medium |
| 13 | If | Medium | Short | | | Medium | Then | High |

FIGURE 27

ANONYMIZED VIDEO ANALYSIS METHODS AND SYSTEMS

CROSS-REFERENCE TO RELATED APPLICATIONS

This application claims the benefit of U.S. Provisional Patent Application entitled "Monitoring System for Eldercare", Ser. No. 61/217,623, filed 1 Jun. 2009, the entire contents of which is herein incorporated by reference.

GRANT STATEMENT

This invention was made with government support under Grant No. IIS-0428420, Grant No. IIS-0703692, and Grant No. CNS-0931607 awarded by the National Science Foundation. The government has certain rights in the invention.

FIELD

This application relates to methods and systems for video analysis, and more specifically to methods and systems for anonymized video analysis.

BACKGROUND

Human activity analysis from video is an open problem that has been studied within the areas of video surveillance, homeland security, and eldercare. Monitoring of human activity may be performed for the assessment of the well-being of a resident and the detection of abnormal or dangerous events.

BRIEF DESCRIPTION OF THE DRAWINGS

FIGS. 17-28 are diagrams, according to example embodiments; and

DETAILED DESCRIPTION

Figure 1:
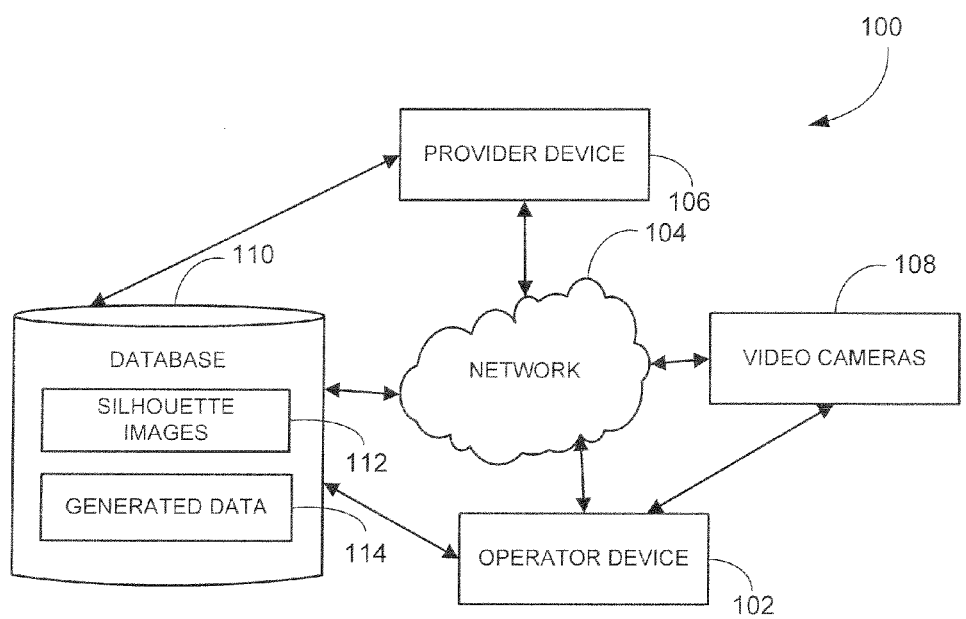
FIG. 1 is a block diagram of an example system, according to an example embodiment.

Example methods and systems for anonymized video analysis are described. In the following description, for purposes of explanation, numerous specific details are set forth in order to provide a thorough understanding of example embodiments. It will be evident, however, to one of ordinary skill in the art that embodiments of the invention may be practiced without these specific details.

The methods and systems may be used to monitor an elderly person's gait in his normal daily environment. To address privacy needs, a silhouette extraction may be used instead of using raw images of the person. The silhouette extraction is generally performed by segmenting the human body from the background with the camera at a fixed location, as the initial stage in the analysis.

A three-dimensional human model, called voxel person, may be constructed in voxel (volume element) space by back projecting silhouettes from multiple camera views. A voxel is a three dimensional volume (a non-overlapping cube) resulting from the discretization of the environment. In some embodiments, the voxel resolution is 1×1×1 inch. In other embodiments, the voxel resolution is 5×5×5 inches. Other resolutions may be used.

Multiple cameras are used to view an environment and the world is quantized into non-overlapping volume elements (voxels). Through the use of silhouettes, a privacy protected image representation of the human, acquired from multiple cameras, a three-dimensional representation of the human is built in real-time and may be referred to as a voxel person. The voxel person may be used to monitor wellbeing of the person in the living unit.

Features may be extracted from the voxel person and fuzzy logic may be used to reason about the membership degree of a predetermined number of states at each frame. In some embodiments, fuzzy logic may enable human activity, which is inherently fuzzy and case based, to be reliably modeled. Fuzzy logic may be used to inferring the state and activity from the person's features. In some embodiments, membership values may provide the foundation for rejecting unknown activities.

The methods and systems may include gait analysis for fall risk assessment in elderly people. There may be a significant correlation between walking speed and physical function, and walking speed may be used as a sole surrogate of the assessment of physical function in the elderly. In addition, elderly people's stride rate tends to increase and their stride length decreases, which may result in a higher risk of falling. A change in the gait profile over time may also indicate that a person is more at risk of falling. The methods and systems may be used as part of an assessment protocol to screen which elderly people are more at risk of falling. Gait training exercises could then be provided, and the effect on their gait could be measured accurately to determine any improvements.

In some embodiments, the methods and systems for anonymized video analysis may help elders live longer, healthier independent lives.

In some embodiments, the methods and systems for anonymized video analysis may be used acquire a fuzzy confidence over time regarding the state of a person from video signal. The video signals may be used for fall detection, a relatively short-time activity, or as part of a framework for higher level reasoning about the person's "well-being" over longer time periods, such as days, weeks, month and even years.

In some embodiments, the methods and systems may be used to monitor functional movements common at a living unit (e.g., a home) in a way that reflects changes in stability and impairment.

FIG. 1 illustrates an example system 100 in which anonymized video analysis may be performed. The system 100 is an example platform in which one or more embodiments of the methods may be used. However, the anonymized video analysis may also be performed on other platforms.

An operator may perform the anonymized video analysis by using the operator device 102. The anonymized video analysis may be performed on a person residing in a living unit. The operator device 102 may be located in the living unit, outside of the living unit but in a living unit community, or a location outside of the living unit community. Examples of operators include clinicians, researchers, family members, the elderly resident, and the like.

The operator may use the operator device 102 as a stand-alone device to perform the anonymized video analysis, or may use the operator device 102 in combination with a provider device 106 available over a network 104. In some embodiments, the provider device 106 is also under the control of the operator but at a location outside of the living unit community.

The operator device 102 may be in a client-server relationship with the provider device 106, a peer-to-peer relationship with the provider device 106, or in a different type of relationship with the provider device 106. In one embodiment, the client-server relationship may include a thin client on the operator device 102. In another embodiment, the client-server relationship may include a thick client on the operator device 102.

The network 104 over which the operator device 102 and the provider device 106 may communicate include, by way of example, a Mobile Communications (GSM) network, a code division multiple access (CDMA) network, an Internet Protocol (IP) network, a Wireless Application Protocol (WAP) network, a WiFi network, or an IEEE 802.11 standards network, as well as various combinations thereof. Other conventional and/or later developed wired and wireless networks may also be used.

In one embodiment, the provider device 106 is a single device. In one embodiment, the provider device 106 may include multiple computer systems. For example, the multiple computer systems may be in a cloud computing configuration.

Multiple video cameras 108 are included in the system 100 to generate video signals of the person residing in the living unit. An example configuration of the video cameras 108 in the living area is described in greater detail below.

The operator device 102, the provider device 106, or both may communicate with a database 110. The database 110 may include silhouette images 112 and generated data 114.

The silhouette images 112 are stored based on the video signals generated by the video cameras 108.

In general, the silhouette images 112 segments the person from an image. The silhouette images 112 may be in the form of a binary map that distinguishes the person from the background.

In some embodiments, the video signals generated by the video cameras 108 prior to converting the images to silhouettes images are not stored in the database 110 or elsewhere in the system 100. The processing performed on the silhouettes images 112 may be stored as the generated data 114 in the database 110.

In some embodiments, the use of the silhouettes images 112 instead of actual images of the person preserves the privacy of the person. The silhouettes may be used to track the person's activity as described in greater detail below.

In some embodiments, the video cameras 108 may be used as component in a larger sensor network. A variety of sensors may be dispersed throughout a living area of the person to capture information such as binary indications of motion in different areas, activity and appliances used in the kitchen, bed sensors for restlessness analysis and more.

Figure 2:
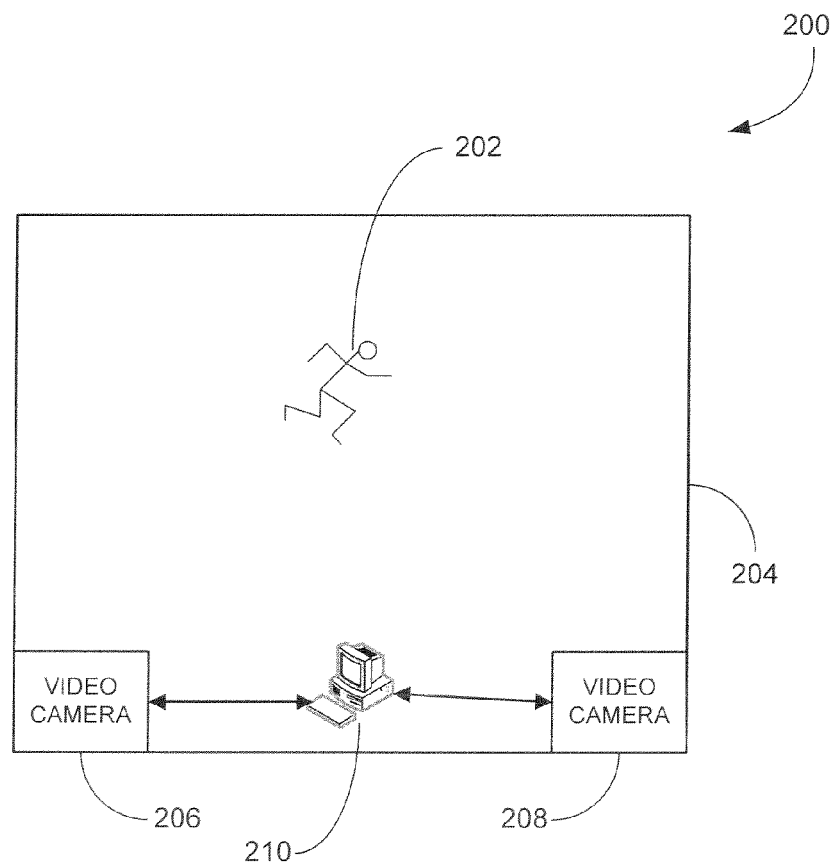
FIG. 2 is a block diagram of an example living unit, according to an example embodiment.

FIG. 2 illustrates an example living unit 200, according to an example embodiment. The living unit 200 is shown to have a person 202 in an area 204 of the living unit 200.

The video cameras 108 of FIG. 1 are shown as two video cameras 206, 208. These video cameras 206, 208 may be deployed in the living unit 200 to generate video signals depicting the person 202 from different views in the area 204. In general, the video cameras 206, 208 include a low end, consumer grade image sensor. For example, the video cameras 206, 208 may be webcams.

In some embodiments, the video cameras 206, 208 consist of two inexpensive web cameras (e.g., Unibrain Fire-i Digital Cameras) that are placed approximately orthogonal to each other in the area 204. In one embodiment, the cameras may capture video at a rate of 5 frames per second with a picture size of 640×480 pixels. Black and white silhouette images are then extracted from the raw videos to maintain the privacy of the person.

In some embodiments, the video cameras 206, 208 are static in the area 204. As such, the video cameras 206, 208 do not move physically locations with the living unit 200, change focus, or otherwise alter its view of the area 204.

In some embodiments, more than two video cameras 206, 208 may be deployed to generate additional video signals of the person 202. The video cameras 206, 208 may then be appropriately deployed in the area 204 or elsewhere in the living unit 200 to generate video signal of the person 202.

In some embodiments, the first video camera 206 is affixed to a first wall of the area 204 and the second video camera 208 is affixed to a second wall of the area 204. The second wall may be an adjacent wall to the first wall in the living unit 200. In general, the video cameras 206, 208 may be affixed in corners of the walls at or near the ceiling.

In some embodiments, the first video camera 206 and the second video camera 208 are approximately 90 degrees apart from each other in the area 204. In some embodiments, the first video camera 206 and the second video camera 208 are between 60 and 89 degrees apart from each other in the area 204. In some embodiments, the first video camera 206 and the second video camera 208 are between 91 and 120 degrees apart from each other in the living unit 200. The video cameras 206, 208 may otherwise be deployed at other angles.

In some embodiments, the use of two video cameras 206, 208 oriented orthogonally with overlapping view volumes results in a silhouette intersection that may be used to define the majority of voxel person's primary shape. The planar extension regions that the person was not occupying are removed by the intersection. The use of more than two cameras may assist with further defining various parts of the body, typically extensions such as arms and feet, as well as eliminating troublesome viewing angles that result in a loss of body detail.

In some embodiments, the use of multiple video cameras 206, 208 may eliminate the limitation of using a controlling walking path to assess the person.

The video signal generated by the video cameras 206, 208 may be provided to the operating device 102 shown in the form of a computing system 210. As shown, the computing system 210 is deployed in the living unit 200. However, the computing system 210 may otherwise be deployed.

The video signals provided by the video cameras 206, 208 may include a number of images of the person 202 or may include a number of silhouette images of the person 202. When the provided video signals include images of the person 202, the computing system 210 may generate the silhouette images of the person 202. When the provided video signals include silhouette images of the person 202, the video cameras 206, 208 may generate the images of the person 202 and generate the silhouette images of the person 202 from the originally generated images. The video cameras 206, 208 may be used to monitor the person in the same scene.

In some embodiments, the 6 DOF location (position and orientation) of each video camera 206, 208 in the area 204 is computed independently using correspondences between a set of 5 or more measured 3D locations in the environment and pixels in the camera image. The 6 DOF location of each video camera 206, 208 is then optimized such that the pixel projection error of the set of 3D points is minimized. Given the optimized location, along with the intrinsic model, the calibrated view vector of each pixel in each video camera 206, 208 can be determined for the purpose of silhouette back projection.

Figure 3:
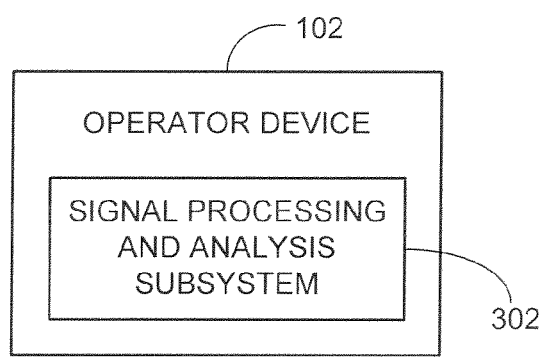
FIG. 3 is a block diagram of an example operator device that may be deployed within the system of FIG. 1, according to an example embodiment.

FIG. 3 illustrates an example operator device 102 that may be deployed in the system 100 (see FIG. 1), or otherwise deployed in another system. The operator device 102 is shown to include a signal processing and analysis subsystem 302 to generate and/or analyze a voxel model of the person 202.

Figure 4:
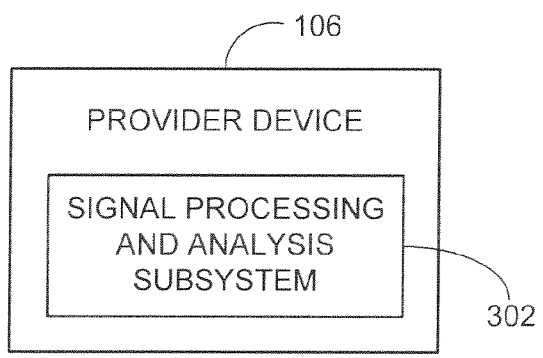
FIG. 4 is a block diagram of an example provider device that may be deployed within the system of FIG. 1, according to an example embodiment.

FIG. 4 illustrates an example provider device 106 that may be deployed in the system 100 (see FIG. 1), or otherwise deployed in another system. The provider device 106 is shown to include a signal processing and analysis subsystem 302 to generate and/or analyze a voxel model of the person 202.

In one embodiment, the voxel model is generated and analyzed solely on the signal processing and analysis subsystem 302 deployed in the operator device 102. In another embodiment, the voxel model is generated and analyzed solely on the signal processing and analysis subsystem 302 deployed in the provider device 106. In another embodiment, the voxel model is generated on the signal processing and analysis subsystem 302 deployed in the operator device 102 and analyzed on the signal processing and analysis subsystem 302 deployed in the provider device 106. In one embodiment, the voxel model is partially generated by the signal processing and analysis subsystem 302 deployed in the operator device 102 and partially generated the signal processing and analysis subsystem 302 deployed in the provider device 106. The voxel model may otherwise be generated and analyzed among the operator device 102, the provider device 106, or another device.

Figure 5:
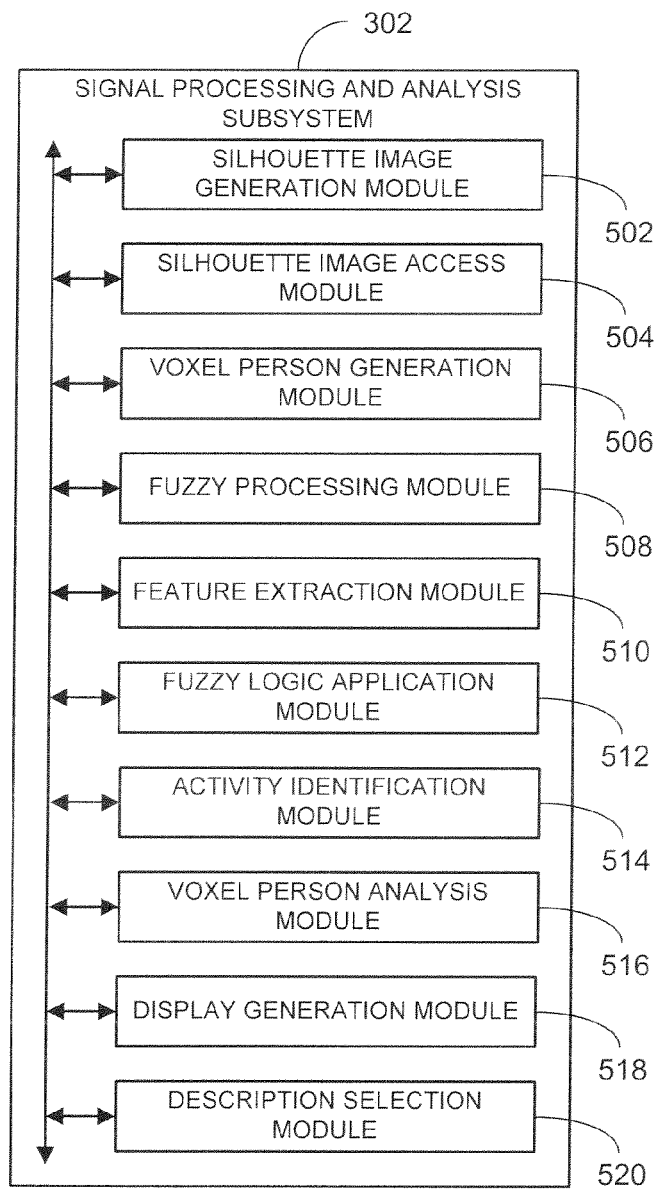
FIG. 5 is a block diagram of an example signal processing subsystem that may be deployed within the operator device of FIG. 3 or the provider device of FIG. 4, according to an example embodiment.

FIG. 5 illustrates an example signal processing and analysis subsystem 302 that may be deployed in the operator device 102, the provider device 106, or otherwise deployed in another system. One or more modules are included in the signal processing and analysis subsystem 302 to generate and/or analyze a voxel model of the person 202. The modules of the signal processing and analysis subsystem 302 that may be included are a silhouette image generation module 502, a silhouette image access module 504, a voxel person generation module 506, a fuzzy processing module 508, a feature extraction module 510, a fuzzy logic application module 512, an activity identification module 514, a voxel person analysis module 516, a display generation module 518, and/or a description selection module 520. Other modules may also be included. In various embodiments, the modules may be distributed so that some of the modules may be deployed in the operator device 102 while other modules may be deployed in the provider device 106. In one particular embodiment, the signal processing and analysis subsystem 302 includes a processor, memory coupled to the processor, and a number of the aforementioned modules deployed in the memory and executed by the processor.

In some embodiments, a silhouette image generation module 502 is deployed in the signal processing and analysis subsystem 302 to generate silhouette images of the person 202 from the video signals. In other embodiments, the silhouette image generation module 502 is deployed in a separate device from the device in which the signal processing and analysis subsystem 302 is deployed. In one embodiment, the silhouette image generation module 502 is deployed in a subsystem of the video cameras 206, 208. In one embodiment, the silhouette image generation module 502 is deployed in the operator device 102 and the remaining modules of the signal processing and analysis subsystem 302 are deployed in the provider device 106. The silhouette image generation module 502 may otherwise be deployed.

In general, the silhouette images are generated based on a video signal received by or generated on a video camera 108. The video signal includes multiple frames or images that generally include a depiction of the person 202 in the area 204 of the living unit 200. The person 202 as depicted may be still or moving in the video signal. The person 202 may also be depicted as departing from or returning to the area 204 in the video signal.

The silhouette image access module 504 accesses silhouette images of the person 202 in the area 204 of the living unit 200. In general, the silhouette images accessed by the silhouette image access module 504 are generated by the silhouette image generation module 502. In one embodiment, the silhouette image access module 504 receives the silhouette images on the provider device 106 from the operator device 102.

Generally, the silhouette image access module 504 accesses two silhouette images of the person 202 in the area 204 of the living unit 200 for an instance in time. The accessed silhouette images are of different views of the person 202 in the area 204. In one embodiment, the silhouette image access module 504 accesses a single silhouette image of the person 202 for the instance in time. In another embodiment, the silhouette image access module 204 accesses more than two different silhouette images of the person 202 for the instance in time.

The voxel person generation module 506 generates a three-dimensional model of the person 202 in voxel space or a voxel person based on at least two silhouette images and viewing conditions of the cameras that generated the original images on which the silhouette images are based.

In some embodiments, the viewing conditions include a location of the first video camera 206 and the second video camera 208 in the area 204, orientation of the first video camera 206 and the second video camera 208, and a lensing effect of the first video camera 206 and the second video camera 208. In one embodiment, the orientation of the first video camera 206 and the second video camera 208 includes a roll, a pitch, and a yaw associated with the first video camera 206 and the second video camera 208.

The silhouette images from a single instance in time or from multiple instances in time may be used by the voxel person generation module 506 to generate the three-dimensional model of the person 202 in voxel space.

In some embodiments, the signal processing and analysis subsystem 302 includes a fuzzy processing module 508 to generate a fuzzified version of the three-dimensional model of the person 202 in the voxel space. In general, the fuzzified version of the three-dimensional model provides a more accurate representation of the person 202 than a non-fuzzified version.

The fuzzy processing module 508 calculates a voxel volume of the three-dimensional model of the person 202, applies fuzzy set theory to the voxel volume of the three-dimensional model of the person 202 based on an expected voxel volume of the person 202, and the generates a fuzzified version of the three-dimensional model of the person 202 in the voxel space based on application of the fuzzy set theory and either the silhouette images and the viewing conditions of the associated video cameras 108 or the non-fuzzified version of the three-dimensional model of the person 202 in the voxel space.

The feature extraction module 510 extracts features from silhouette images of the person 202 and/or the three-dimensional model of the person 202, or both. The feature extraction module 510 may extract a single feature or multiple features from the silhouette images and/or the three-dimensional model of the person 202. In general, a feature describes an aspect of the person 202. Examples of features include height of the three-dimensional model of the person 202, a centroid of the three-dimensional model of the person 202, and a ground plane normal similarity of the three-dimensional model of the person 202. Other or different features of the person 202 may be extracted.

In some embodiments, the extraction of features from the voxel person by the feature extraction module 510 may be used to determine a current state of the person.

The fuzzy logic application module 512 applies fuzzy logic to extraction of the features extracted by the feature extraction module 510 to identify a state of the person 202.

In some embodiment, the activity identification module 514 identifies an activity of the person 202. The activities may be identified based on states identified by the fuzzy logic application module 512 in a single version or different versions of the three-dimensional model of the person 202, features of the three-dimensional model of the person 202 or transitions of features between different versions of the three-dimensional model of the person 202, or may otherwise be identified. For example, the activity identification module 514 may identify a falling activity when the three-dimensional model of the person 202 transitions from an upright state to an on-the-ground state and includes a certain transition of some of the features between versions of the three-dimensional model of the person 202 at different instances in time.

The voxel person analysis module 516 analyzes aspects (e.g., features) of the three-dimensional model of the person 202 to obtain a result. A single aspect or multiple aspects of the three-dimensional model of the person 202 may be analyzed to obtain a single result or multiple results.

In some embodiments, the voxel person analysis module 516 analyzes a centroid of the three-dimensional model of the person 202 during a time period and calculates a speed of the person 202 during the time period based on the analysis of the centroid.

In some embodiments, the voxel person analysis module 516 analyzes a projection of a bottom section of the three-dimensional model of the person 202 onto a ground plane of the living unit 200 during a time period. The voxel person analysis module 516 may then calculate step length and step time during a time period based on the analysis of the projection. Step time is generally the time elapsed from first contact of one foot to the first contact of the opposite foot. The step length of the right foot is generally the distance between the center of the left foot to the center of the right foot along the line of progression.

In some embodiments, the voxel person centroid is the average of all the voxels locations. The centroid represents the 3D location of the person at a given time. The distance the person traveled in 2D space may be approximated by voxel person analysis module 516 by adding up the distance the centroid location moved at each frame of the video signals. Walking speed may be calculated by the voxel person analysis module 516 based on the distance traveled divided by time calculated from the frame rate and the number of frames.

The voxels in a bottom section (e.g., with a height below 4 inches) from the ground plane may be used to capture foot motion. They may be projected onto the 2D space. As shown in the FIG. 20 below, the solid line may represent the length from the front of one foot to the end of the other foot. It may be projected along the walking direction. The walking direction may be obtained from the centriod in consecutive frames. The length may alternatively expands (shown as peaks) and contracts (shown as valleys) over time as the person's feet spread and close during the gait cycle. The number of steps may be obtained directly from the number of peaks representing the number of gait cycles. The average step time may then be calculated as the total time divided by the number of steps. The step length may then be calculated as a function of the step time and walking speed.

In some embodiments, the voxel person analysis module 516 analyzes a projection of a bottom section of the three-dimensional model of the person 202 onto a ground plane of the living unit 200 during a time period, identifies voxel intersections during the time period, and forms spatial clusters based on identification of the voxel intersections to identify footsteps of the person 202 during the time period.

The voxel person analysis module 516, in some embodiments, identifies or otherwise determines a direction of motion and/or a left footstep, a right footstep, a left step length, a right step length, a left step time, a right step time, and/or shuffling based on the footsteps. Other results may be identified or otherwise determined from the footsteps.

The voxel person analysis module 516 may be used to determine footfalls. For example, the extraction from voxel data may based on the assumption that during walking, one foot will remain stationary while the other foot is in motion. Voxels below two inches may be used to capture information about the feet. Thus, the footfall extraction process performed by the voxel person analysis module 516 may be based on identifying 2D locations that are contained in the projection, of voxels below two inches onto the ground plane for a minimum number of consecutive frames. Such 2D locations may have a high likelihood of corresponding to a footfall.

In some embodiments, the voxel person analysis module 516 accesses a centroid of the three-dimensional model of the person 202, computes a trajectory of the three-dimensional model of the person 202 over a time period, generates a varying angle and an amplitude of the three-dimensional model of the person 202 based on the certroid and computation of the trajectory, and identifies lateral sway of the three-dimensional model of the person 202 based on generation of the varying angle and the amplitude.

In some embodiments, the voxel person analysis module 516 accesses a centroid of the three-dimensional model of the person 202, determines a base of support of the three-dimensional model of the person 202, generates a varying angle and an amplitude of the three-dimensional model of the person 202 based on the certroid and the base of the support, and identifies body sway of the three-dimensional model of the person 202 based on generation of the varying angle and the amplitude.

In some embodiments, the feature extraction module 510 extracts a single feature or multiple features from the silhouette images of the person 202 and extracts a singe feature or multiple features from the three-dimensional model of the person 202. The voxel person analysis module 516 may then identify sit to stand time of the person 202 based on the extraction of the features from multiple versions of the three-dimensional model of the person 202 and multiple silhouette images of the person 202 on which the three-dimensional model of the person 202 was based. In general, the multiple versions are associated with frames of the video signals that encompassed the person sitting, the person standing, and the in-between frames.

The display generation module 518 generates a display of the three-dimensional model of the person 202. The display includes a silhouetted depiction of the three-dimensional model in the living unit 200.

In some embodiments, multiple three-dimensional models of the person 202 in voxel space during a time period are generated by the voxel person generation module 506. The voxel person analysis module 516 analyzes the three-dimensional models of the person 202 to identify states of the person 202 during the time period. A single state or multiple states of the person 202 may be identified. The description selection module 520 selects a description based on analysis of the three-dimensional models by the voxel person analysis module 516 and the display generation module 520 generates a display that includes the description. A description may be associated with each state identified. The description may include identification of the states. In one embodiment, the voxel person analysis module 516 may analyze the three-dimensional models of the person 202 to identify movement of the person 202 through the living unit 200 during the time period. The description may also be associated with the identified movement.

Figure 6:
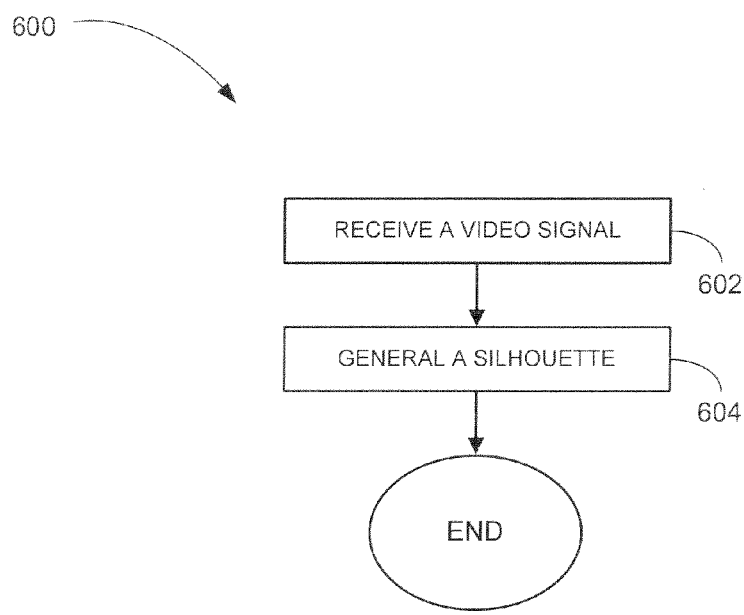
FIG. 6 is a block diagram of a flowchart illustrating a method for silhouette image generation, according to an example embodiment.

FIG. 6 illustrates a method 600 for silhouette image generation according to an example embodiment. The method 600 may be performed by the operator device 102 or the analysis device 106 of the system 100 (see FIG. 1), or may be otherwise performed.

A video signal is received from a video camera at block 602. The first video signal includes multiple frames that include a depiction of the person 202 in the area 204 of the living unit 200.

A silhouette image of the person 202 is generated from the video signal at block 604. In general, the silhouette image is based on a single frame or image taken from the video signal received at block 602.

Silhouette generation or extraction, namely, involves segmenting the human from an image with the video camera at a fixed location. In general, a background model and regions in subsequent images with significantly different characteristics are classified as foreground. The differencing task is usually formalized as a background subtraction procedure. In some embodiments, an adaptive method for background subtraction that uses a mixture of Gaussians per pixel or per region of pixels with a real-time online approximation to the model update may be used.

The method 600 may be performed a single time or may be performed multiple times. For example, the method 600 may be performed on a number of frames of several video signals to generate multiple silhouette images from each video signal.

The method may be performed on simultaneously (or nearly simultaneously) on multiple video signals to generate corresponding silhouette images of the person 202 from different views in the area 204 of the living unit 200.

By way of example, a first video signal may be received from the first video camera 206, a second video signal may be received from the second video camera 208, the second video signal including a different depiction of the person 202 than the depiction of the person in the first video signal, a first silhouette image of the person may be generated from the first video signal and a second silhouette image of the person may be generated from the second video signal.

When the method 600 is performed by the video cameras 206, 208, the video signal may be generated instead of being received.

Figure 7:
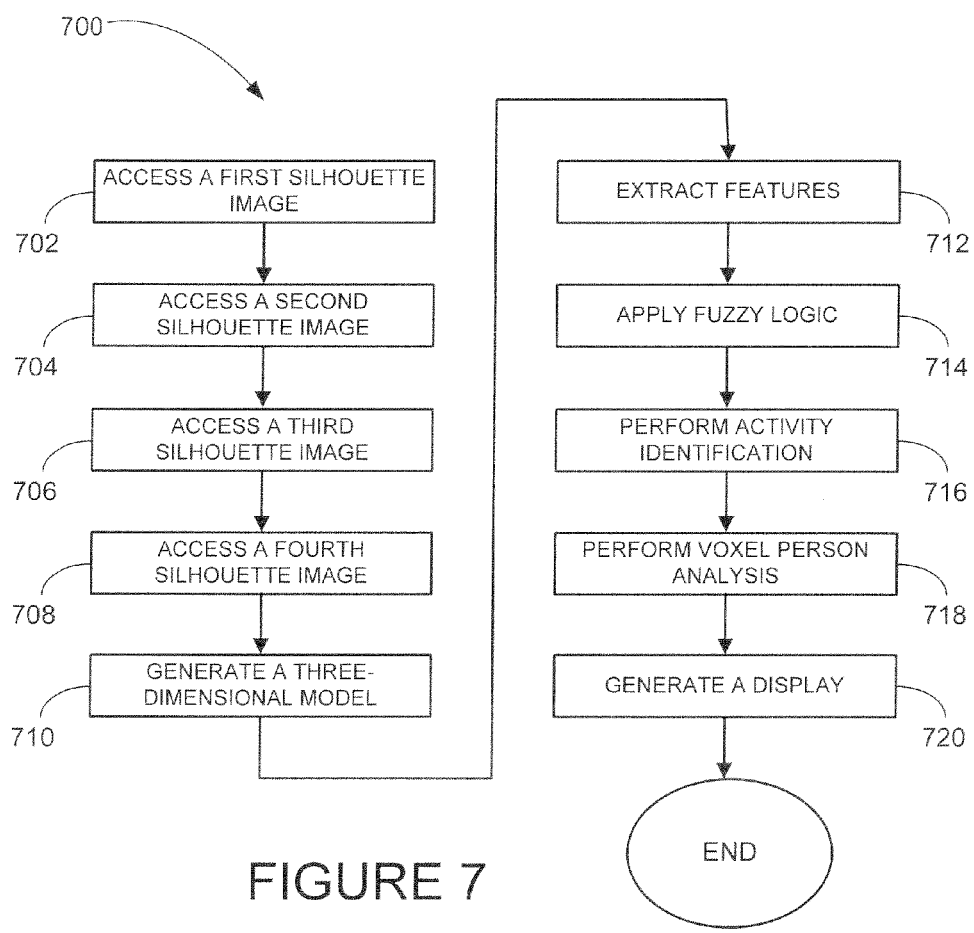
FIGS. 7 and 8 are block diagrams of flowcharts illustrating methods for three-dimensional model generation, according to an example embodiments.

FIG. 7 illustrates a method 700 for three-dimensional model generation according to an example embodiment. The method 700 may be performed by the operator device 102 or the provider device 106 of the system 100 (see FIG. 1), or may be otherwise performed.

A first silhouette image of a person 202 in the living unit 200 is accessed at block 702. The first silhouette image is based on a first video signal recorded by a first video camera 206.

A second silhouette image of the person 202 in the living unit 200 is accessed at block 704. The second silhouette image is of a different view of the person 202 than the first silhouette image. The second silhouette image is based on a second video signal recorded by a second video camera 208. The first video camera 206 and the second video camera 208 are positioned to record the area 204 of the living unit 200 from a different position in the living unit 200.

In general, the first silhouette image and the second silhouette image are associated with the person 202 in a same position in the area 204 and the first silhouette image and the second silhouette image are associated a similar or same moment in time.

A third silhouette image of the person 202 in the living unit 200 may be accessed at block 706. The third silhouette image is based on the first video signal recorded by the first video camera 206. The third silhouette image is associated with a different frame of the first video signal than the first silhouette image.

A fourth silhouette image of the person 202 in the living unit 200 may be accessed at block 708. The fourth silhouette image is based on the second video signal recorded by the second video camera 208. The fourth silhouette image is associated with a different frame of the second video signal than the second silhouette image.

At block 710, a three-dimensional model of the person 202 in voxel space is generated. In some embodiments, the three-dimensional model of the person 202 is generated based on the first silhouette image, the second silhouette image, and viewing conditions of the first video camera 206 and the second video camera 208.

The viewing conditions may include, by way of example, a location of the first video camera 206 and the second video camera 208 in the living unit 200, orientation of the first video camera 206 and the second video camera 208, and a lensing effect of the first video camera 206 and the second video camera 208.

In some embodiments, generation of the three-dimensional model of the person 202 in voxel space is based on the first silhouette image, the second silhouette image, the third silhouette image, the first silhouette image, and viewing conditions of the first video camera 206 and the second video camera 208.

In some embodiments, the three-dimensional model of the person 202 in voxel space is generated for multiple instances in time based on the accessed silhouette images. For example, the three-dimensional model of the person 202 generated from the first silhouette image, the second silhouette image, and the viewing conditions may be associated with a first time instance in a time period and the three-dimensional model of the person 202 generated from the third silhouette image, the fourth silhouette image, and the viewing conditions of the first video camera 206 and the second video camera 208 may be associated with a second time instance (e.g., later in time) in the time period.

A three-dimensional representation or model of the person 202 constructed or generated in voxel space is associated with a number of voxels. In general, a voxel (volume element) is an element resulting from a discretization of three-dimensional space. Voxels are typically non-overlapping cubes.

In some embodiments, each image from the video signal has a capture time recorded. The silhouettes for of the video cameras 108 that are the closest in time are used to build the current voxel person. Construction of voxel person from a single camera results in a planar extension of the silhouette along the direction of the camera viewing angle. Voxels in the monitored space that are intersected by this planar extension may be identified. The planar extensions of voxel person from multiple cameras are combined using an operation, such as intersection, may be used to assemble a more accurate object representation.

In some embodiments, the voxel person is a relatively low resolution object for computational efficiency. In some embodiments, the voxel person is not explicitly tracked, segmentation of object regions of the voxel person is not attempted, and the voxel person does not have a highly detailed surface or solid representation. In some embodiments, voxels that correspond to walls, floor, ceiling, or other static objects or surfaces are removed.

Features from the three-dimensional model of the person 202 may be extracted at block 712. The features may be spatial, temporal, or both spatial and temporal. The spatial features include voxel person's (a) centroid, (b) eigen-based height, and (c) the similarity of voxel person's primary orientation and the ground plane normal.

In some embodiments, the features extracted from voxel person are used to determine a current state of the person. A finite set of states may be identified ahead of time and membership degrees of each state may be determined at every time step or image. These state membership degrees may then be input to activity analysis.

An activity may be modeled according to specific state duration, frequency of state visitation, and state transition behavior. The collection of states, for fall recognition may include upright, on-the-ground, and in-between.

The upright state is generally characterized by voxel person having a large height, its centroid being at a medium height, and a high similarity of the ground plane normal with voxel person's primary orientation. Activities that involve this state are, for example, standing, walking, and meal preparation.

The on-the-ground state may be generally characterized by voxel person having a low height, a low centroid, and a low similarity of the ground plane normal with voxel person's primary orientation. Example activities include a fall and stretching on the ground.

The in-between state is generally characterized by voxel person having a medium height, medium centroid, and a non-identifiable primary orientation or high similarity of the primary orientation with the ground plane normal. Some example activities are crouching, tying shoes, reaching down to pick up an item, sitting in a chair, and even trying to get back up to a standing stance after falling down.

Each feature may be used to determine a degree to which the voxel person is in a particular state.

At block 714, fuzzy logic may be applied to extraction of the features to identify a state of the person 202. In one embodiment, the application of fuzzy logic includes use of the standard Mamdani fuzzy inference system.

Activity identification of the three-dimensional model of the person 202 may be performed at block 716.

Voxel person analysis may be performed on the three-dimensional model of the person 202 at block 718.

A display of the three-dimensional model of the person 202 may be generated at block 720. The display may include a silhouetted depiction of the three-dimensional model of the person 202 in the living unit 200.

Figure 8:
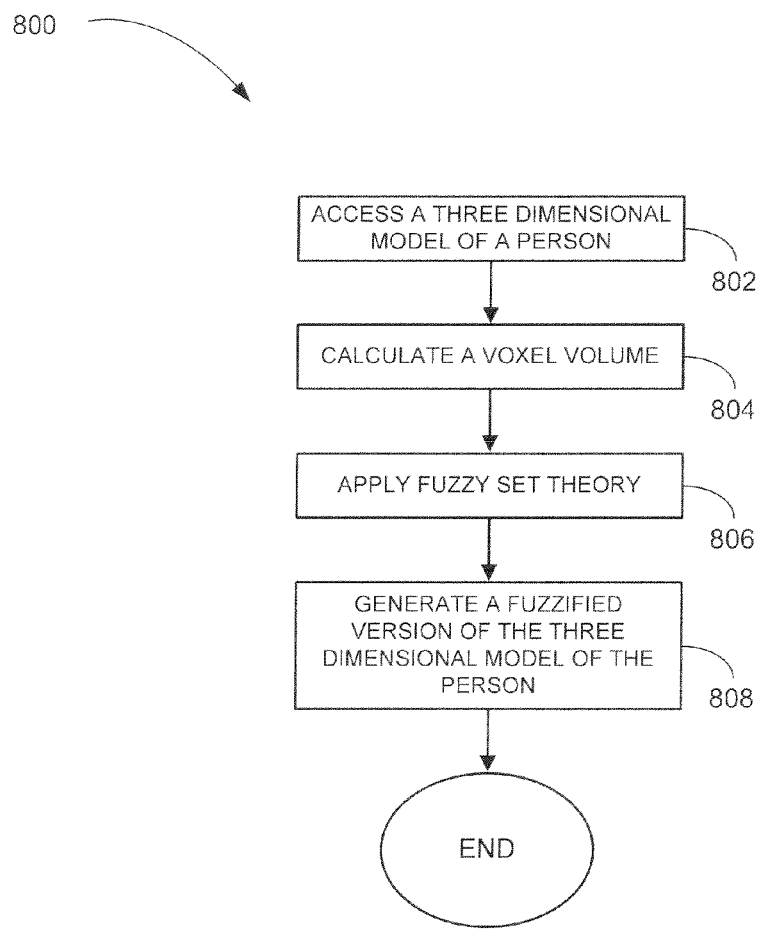

FIG. 8 illustrates a method 800 for three-dimensional model generation according to an example embodiment. The method 800 may be performed by the operator device 102 or the provider device 106 of the system 100 (see FIG. 1), or may be otherwise performed.

A three dimensional model of the person 202 may be accessed at block 802. The three dimensional model of the person 202 may be generated by the method 700, or may otherwise be generated.

A voxel volume of the three-dimensional model of the person 202 is calculated at block 804. In some embodiments, the volume of voxel person can be approximated by summing up the number of voxels. In some embodiments, the voxel volume can be calculated through generating the covariance matrix for voxel person and computing its determinant.

At block 806, fuzzy set theory is applied to the voxel volume of the three-dimensional model of the person 202 based on an expected voxel volume of the person 202. In general, the fuzzy set theory may is used in the method 800 for modeling features extracted from the person 202, the person's state and the person's subsequent activity.

A fuzzified version of the three-dimensional model of the person 202 in the voxel space is generated at block 808. The fuzzified version of the three-dimensional model is based on the silhouette images used to generate the three dimensional model of the person 202 accessed at block 802, the viewing conditions of the video cameras 108 used to record the video signals on which the silhouette images were based, and application of fuzzy set theory.

Figure 9:
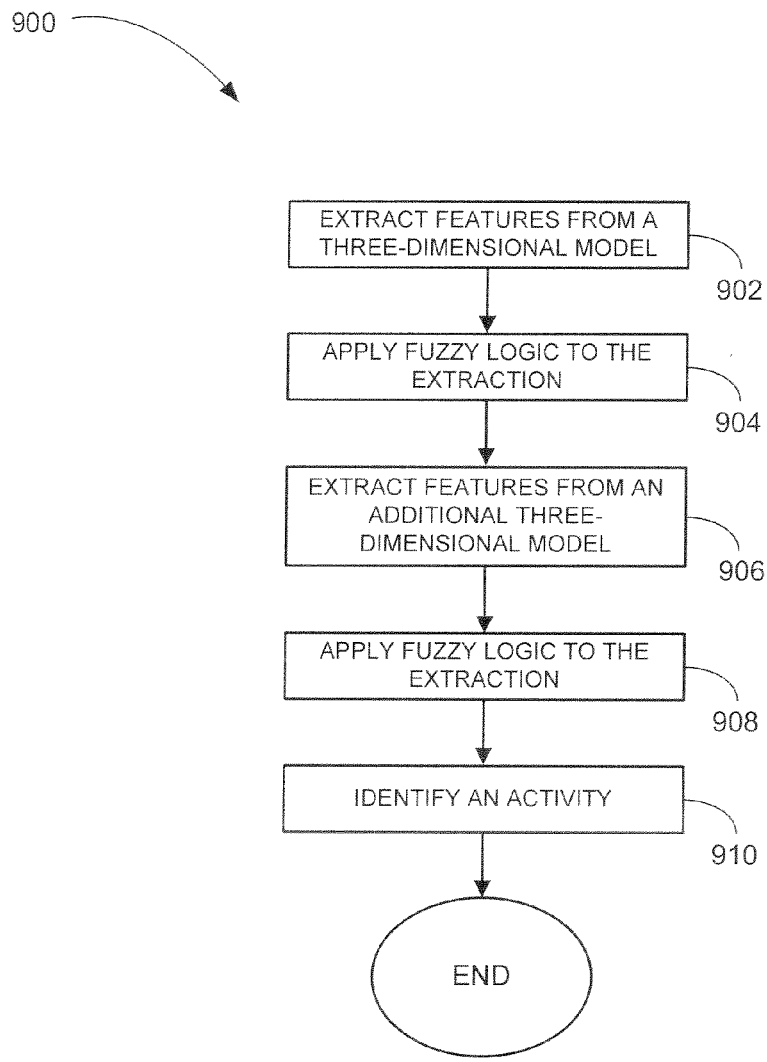
FIG. 9 is a block diagram of a flowchart illustrating a method for activity identification, according to an example embodiment.

In some embodiments, fuzzified version of the three-dimensional model of the person 202 may reflect the persons's profile, such as their height, width, and length, FIG. 9 illustrates a method 900 for activity identification according to an example embodiment. The method 900 may be performed at block 716 (see FIG. 7), or may be otherwise performed.

Features are extracted from the three-dimensional model of the person 202 at block 902. The three-dimensional model may be based on a first silhouette image and a second silhouette image.

At block 904, fuzzy logic is applied to extraction of the features from the three-dimensional model of the person 202 to identify a first state of the person 202.

Features are extracted from an additional three-dimensional model of the person 202 at block 906. The additional three-dimensional model may be based on a third silhouette image of the person 202 in the living unit 200 and a fourth silhouette image of the person 202 in the living unit 200. The third silhouette image is associated with a different frame of the first video signal than the first silhouette image. The fourth silhouette image is based on the second video signal recorded by the second video camera. The fourth silhouette image is associated with a different frame of the second video signal than the second silhouette image.

At block 908, fuzzy logic is applied to the extraction of the features from the additional three-dimensional model of the person 202 to identify a second state of the person 202.

An activity of the person 202 is identified as a falling activity at block 910 when the three-dimensional model of the person 202 transitions from an upright state to an on-the-ground state between the first state and the second state and includes a certain transition from the three-dimensional model of the person 202 to the additional three-dimensional model of the person 202 for at least some of the plurality of features.

Figure 10:
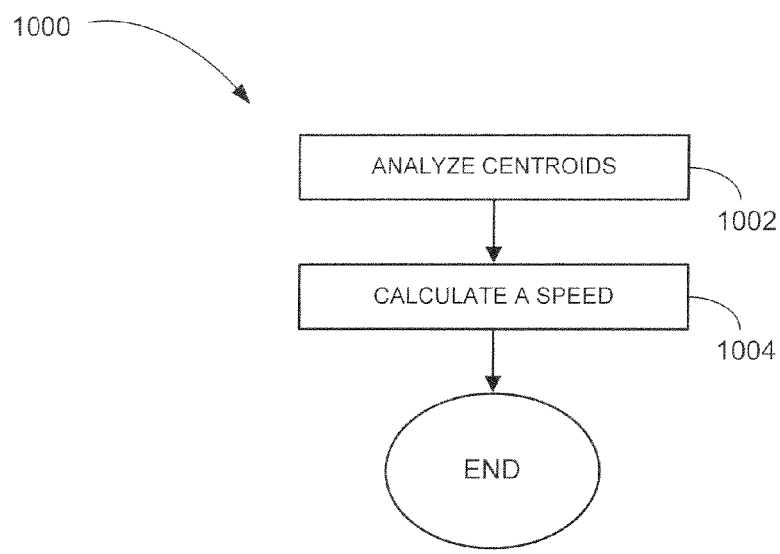
FIGS. 10-15 are block diagrams of flowcharts illustrating methods for voxel person analysis, according to example embodiments.

FIG. 10 illustrates a method 1000 for voxel person analysis according to an example embodiment. The method 1000 may be performed at block 718 (see FIG. 7), or may be otherwise performed. The method 1000 may be used to determine the speed of the voxel person.

The centroids of the three-dimensional model of the person 202 during the time period are analyzed at block 1002. In some embodiments, the analysis includes analyzing the motion of the centroid of the person 202 during the time period. In some embodiments, the analysis includes analyzing s sequence of the centroids. Other types of analysis may be performed that may be used to calculate speed.

At block 1004, a speed of the person 202 during the time period is calculated based on the analysis of the centroids.

Figure 11:
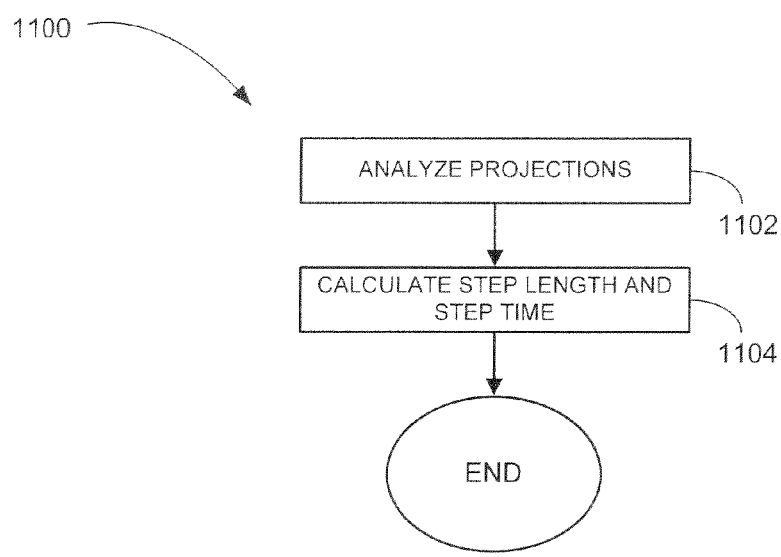

FIG. 11 illustrates a method 1100 for voxel person analysis according to an example embodiment. The method 1100 may be performed at block 718 (see FIG. 7), or may be otherwise performed. The method 1100 may be used to determine step length and step time of the voxel person.

At block 1102, projections of a bottom section of the three-dimensional model of the person 202 onto a ground plane of the living unit 200 during the time period are analyzed. In some embodiments, the projections are a sequence of projections.

Step length and step time during the time period is calculated at block 1104 based on the analysis of the projections.

Figure 12:
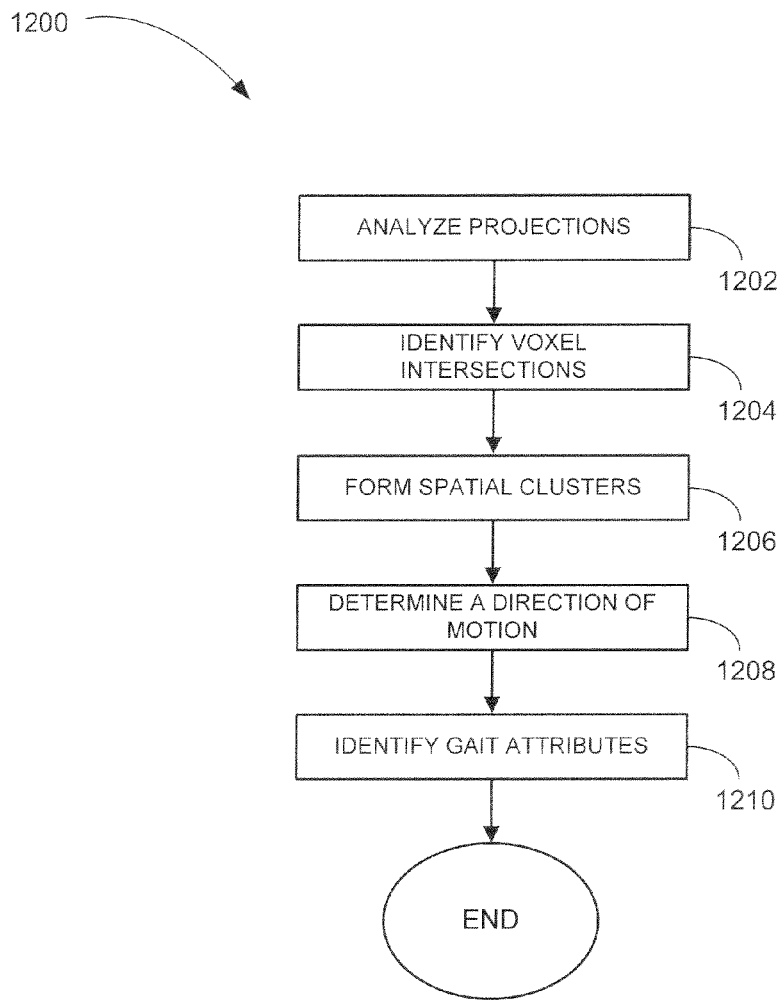

FIG. 12 illustrates a method 1200 for voxel person analysis according to an example embodiment. The method 1200 may be performed at block 718 (see FIG. 7), or may be otherwise performed.

Projections of a bottom section of the three-dimensional model of the person 202 onto a ground plane of the living unit 200 during the time period are analyzed at block 1202. In some embodiments, the projections are a sequence of projections.

At block 1204, voxel intersections are identified during the time period. In general, a voxel intersection includes an overlapping portion of the bottom section of the three-dimensional model of the person 202 onto the ground plane on consecutive frames of a video signal from which the silhouette images were taken.

Spatial clusters are formed at block 1206 based on identification of the voxel intersections to identify footsteps of the person 202. A footstep is associated with a spatial cluster.

At block 1208, a determination of a direction of motion of the three-dimensional model of the person 202 may be made based on the footsteps.

Gait attributes may be identified at block 1210 based on the footsteps. For example, a left footstep, a right footstep, a left step length, a right step length, a left step time, a right step time, and shuffling may be identified.

Figure 13:
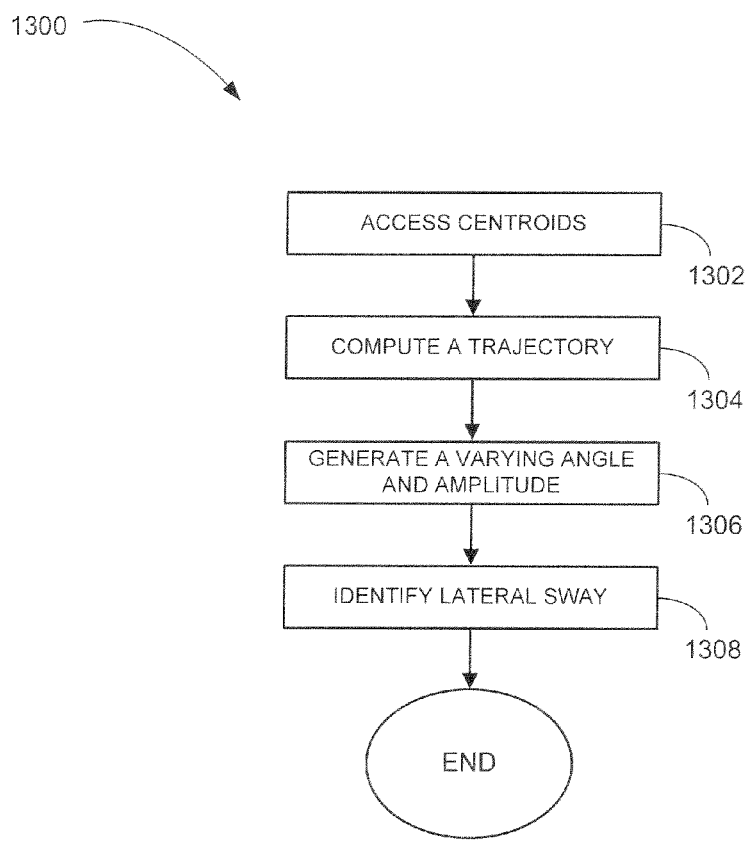

FIG. 13 illustrates a method 1300 for voxel person analysis according to an example embodiment. The method 1300 may be performed at block 718 (see FIG. 7), or may be otherwise performed.

Centroids of the three-dimensional model of the person 202 over a time period are accessed at block 1302. In some embodiments, the centroids are associated with a sequence of images. A trajectory of the three-dimensional model of the person 202 over the time period is computed at block 1304.

At block 1306, a varying angle and amplitude of the three-dimensional model of the person 202 is generated based on the certroids and computation of the trajectory.

Lateral sway of the three-dimensional model of the person 202 is identified at block 1308 based on generation of the varying angle and the amplitude.

Figure 14:
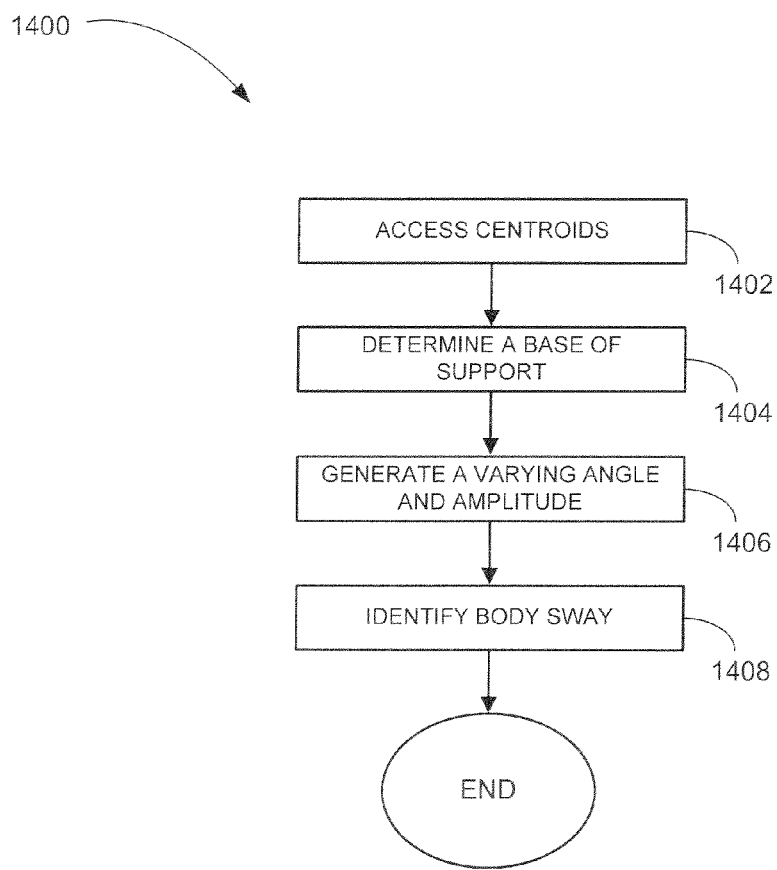

FIG. 14 illustrates a method 1400 for voxel person analysis according to an example embodiment. The method 1400 may be performed at block 718 (see FIG. 7), or may be otherwise performed. The method 1400 may be used to determine body sway of the person.

Body sway during standing includes sway in lateral and anterior-posterior directions. Body centroid ($x_{ctr}$, $y_{ctr}$, $z_{ctr}$) may be estimated using the voxel person. A fixed mid-point ($x_{ref}$, $y_{ref}$) may be computed from the mean of centroid positions, and selected as a reference point on the ground plane for the base of support with $z_{ref}=0$. The sway distance/amplitude may be computed as the distance between the body centroid projection onto the ground plane and the reference point in 2-D space as: $d=\sqrt{(x_{ctr}-x_{ref})^2-(y_{ctr}-y_{ref})^2}$ where x and y are the coordinate positions in the anterior-posterior (x) and lateral (y) directions.

In some embodiments, the use of 3D voxel data may eliminate the limitation of a controlled walking path and enable the use of the method for determining body sway for daily assessment in the home environment (e.g., the living unit 200).

Centroids of the three-dimensional model of the person 202 during a time period are accessed at block 1402. In some embodiments, the centroids are associated with a sequence of images. A determination of a base of support of the three-dimensional model of the person 202 is made at block 1404.

At block 1406, a varying angle and an amplitude of the three-dimensional model of the person 202 based on the centroids and the base of the support.

Body sway of the three-dimensional model of the person 202 is identified at block 1408 based on generation of the varying angle and the amplitude.

Figure 15:
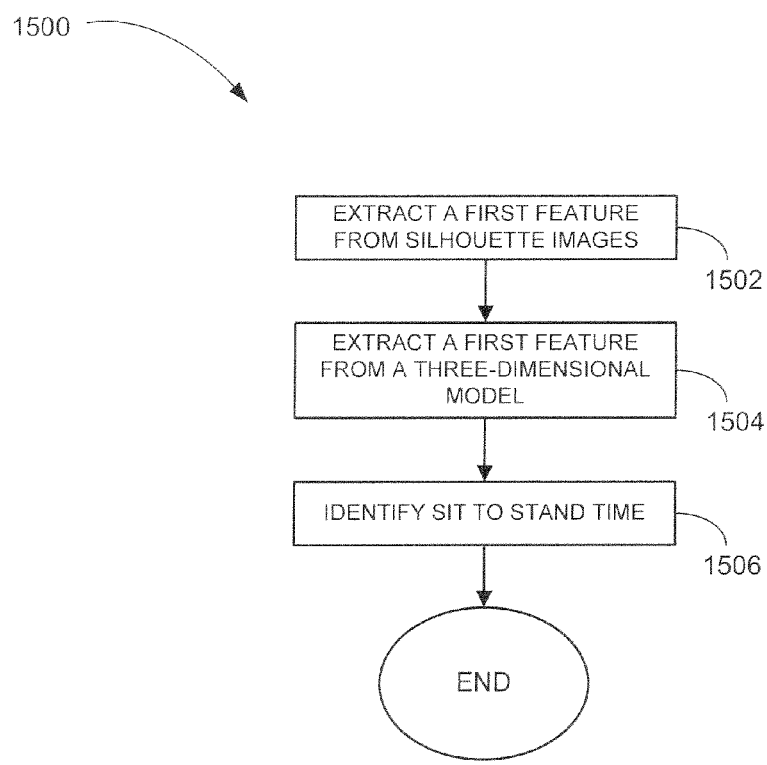

FIG. 15 illustrates a method 1500 for voxel person analysis according to an example embodiment. The method 1500 may be performed at block 718 (see FIG. 7), or may be otherwise performed. The method 1500 may be used to determine sit to stand time.

In some embodiments, the method 1500 may use a set of Hu moments. In general, the Hu moments are a set of seven central moments taken around the weighted image center. In some embodiments, the first three Hu moments may be used with the method 1500. In other embodiments, the method 1500 may use a set of Zernike moments.

Fuzzy clustering techniques may be used with the method 1500 to partition data on the basis of their closeness or similarity using fuzzy methods. In some embodiments, Gustafson Kessel and Gath and Geva fuzzy clustering techniques may be implemented on image moments.

A first feature is extracted from the multiple silhouette images associated with the first video camera 206 and multiple silhouette images associated with the second video camera at block 1502. A second feature is extracted from multiple versions of the three-dimensional model of the person 202 at block 1504. In general, the multiple silhouette images and multiple versions of the three-dimensional model of the person 202 are associated with multiple frames of the video signals during which the person transitioned from sit to stand.

At block 1506, sit to stand time is identified based on extraction of the first feature and the second feature.

Figure 16:
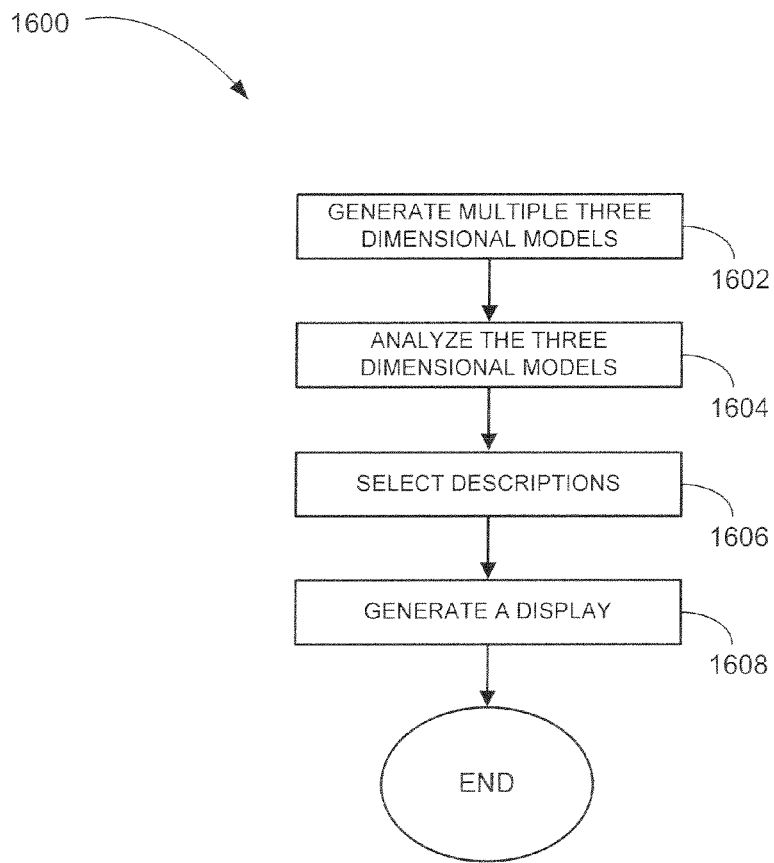
FIG. 16 is a block diagram of a flowchart illustrating a method for description selection, according to an example embodiments.

FIG. 16 illustrates a method 1600 for description selection according to an example embodiment. The method 1600 may be performed by the operator device 102 or the provider device 106 of the system 100 (see FIG. 1), or may be otherwise performed. The method 1600 may be used to create linguistic summarization of video for fall detection.

The method 1600 may generate a significantly smaller number of rich linguistic summaries of the person's state over time, in comparison to the large number of state decisions made at each image. The method 1600 includes a procedure that may be used to infer activity from features calculated from linguistic summarizations. In some embodiments, summarization and activity inference improves fall detection.

The method 1600 may use the result of reasoning about the state of voxel person at time. For example, the three membership values corresponding to the confidence of being upright, in-between, and on-the-ground may be used. Although decisions regarding activity may be made at each image from the state memberships, the result may be too much information for practical use in some embodiments. The method 1600 may takes seconds, minutes, hours, and even days of the person's activity to produce succinct linguistic summarizations, such as "the resident was preparing lunch in the kitchen for a moderate amount of time" or "the resident has fallen in the living room and is down for a long time".

Linguistic summarization may increase the understanding of the system output, and produce a reduced set of salient descriptions that characterizes a time interval. The linguistic summarizations may assist in informing nurses, persons, persons' families, and other approved individuals about the general welfare of the persons, and they are the input for the automatic detection of cognitive or functional decline or abnormal event detection.

The method 1600 may use a single linguistic variable over the time domain that has the following terms, specified in seconds, with corresponding trapezoidal membership functions: brief=[_1 1 1 2], short=[1 5 10 15], moderate=[10 120 480 720], and long=[480 900 86400 86400]. Other terms may be used.

In operation, the method 1600 includes generation of multiple three-dimensional models of a person 202 in voxel space for a time period at block 1602.

The three-dimensional models are analyzed at block 1604 to identify states of the person 202 during the time period, movement of the person 202 through the living unit 200 during the time period, or both. In some embodiments, the description includes identification of the first state and the second state. In one embodiment, the first state is a different state then the second state. In one embodiment, the first state is a same state as the second state.

Descriptions are selected at block 1606 based on analysis of the three-dimensional models.

A display including the description may be generated at block 1608.

Figure 17:
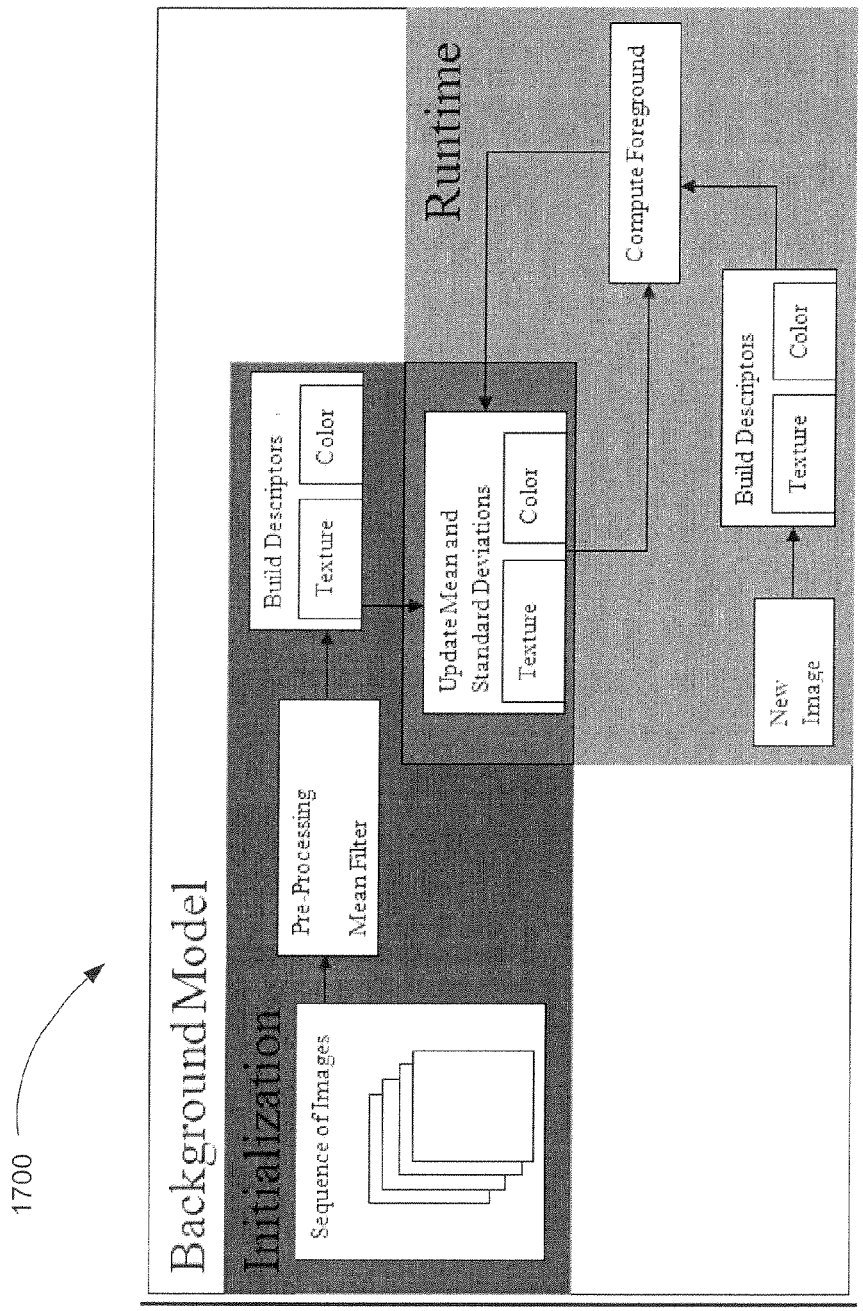
Figure 18:
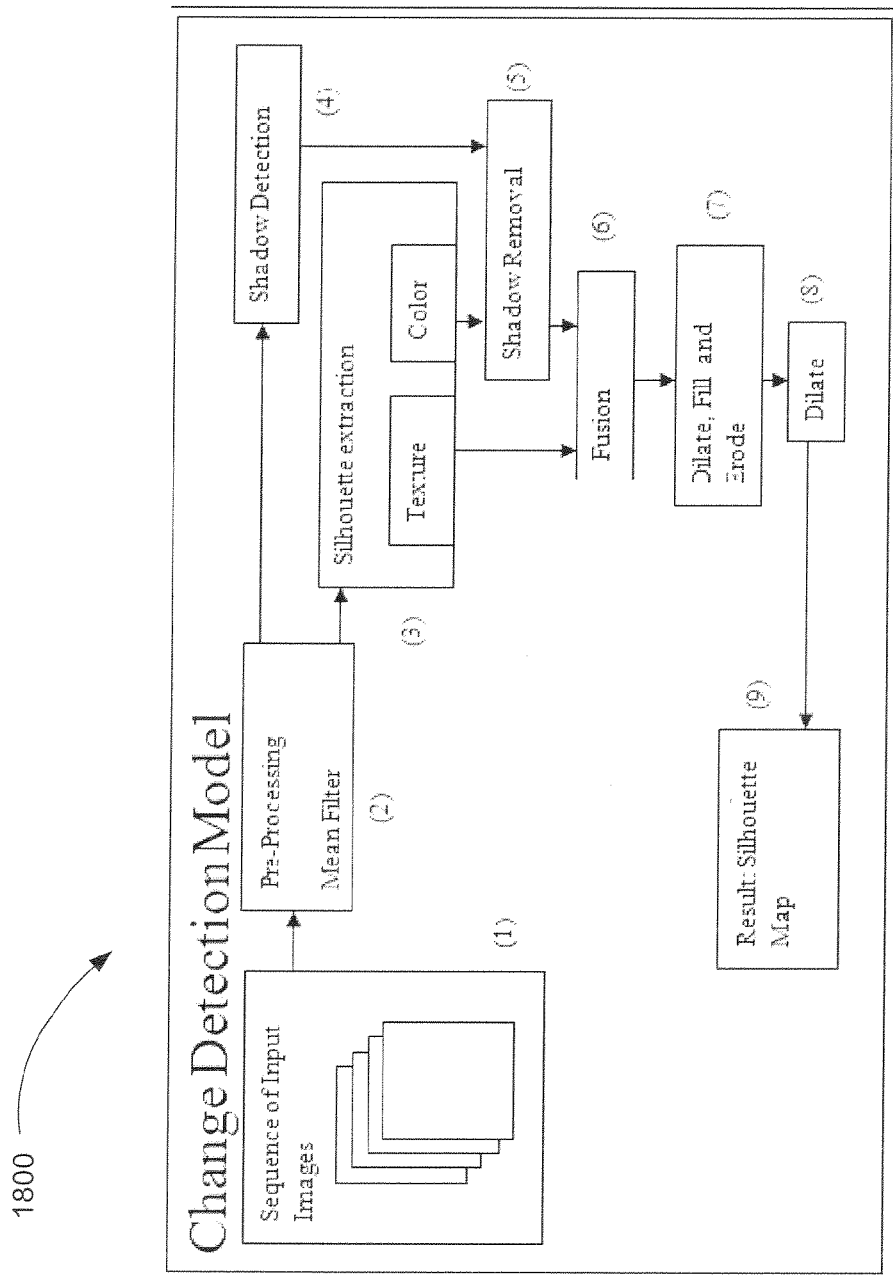

FIG. 17 illustrates a block diagram of a background model 1700, according to an example embodiment. FIG. 18 illustrates a block diagram of a change detection model 1800, according to an example embodiment.

Silhouette segmentation or extraction is a change detection procedure. Before silhouette extraction can occur, an accurate background model is typically acquired. The background model 1700 is generally defined as any non-human, static object.

As each new image from the video signal is acquired, features are extracted and locations that have significantly changed from the background are identified. In some embodiments, the silhouette extraction described between the background model 1700 and the change detection model 1800 is adaptive, incorporates both texture and color information, and performs shadow removal.

The background model 1700 may be first built using a user specified number of images (e.g., around 10 frames). Other numbers of images may be used. In some embodiments, the silhouette extraction described between the background model 1700 and the change detection model 1800 is adaptive and may use less than 10 frames of the video signal to initialize the background model 1700. For example, a lesser sequence of images that contain only the background and not the human may be used.

After the background model 1700 is initialized, regions in subsequent images with significantly different characteristics from the background are considered as foreground objects. Areas classified as background are also used to update the background model. Fused texture and color features are used for background subtraction.

The silhouette extraction described between the background model 1700 and the change detection model 1800 may pre-process images for pixel noise removal. Color and texture features based on histograms of texture and color may be extracted. The mean and standard deviation of a single Gaussian may be recorded for each pixel. Each new image may then be passed through the change detection model 1800.

The images are pre-processed; shadows may be removed using a modified Hue, Saturation, and Value (HSV) color space procedure. In general, the hue is the perceived color, saturation describes the amount of color present, and value is related to brightness. Color and texture features may be extracted. Shadows may be removed from the color features, which have a greater tendency to register shadows given the selected color space and feature descriptor, the texture results, which are computed using different color spaces, may be fused using the Yager union, then morphological and logical operations may be performed on the results to remove noise and clean up the silhouette. Morphological dilation may be performed in order to expand areas of the silhouette (e.g., to assist in the creation of connected silhouettes). A fill operation may take the dilated result and make regions that are surrounded by a connected silhouette region foreground. Lastly, these results may be eroded to reduce them to a size and shape that is more like the original silhouette.

Figure 19:
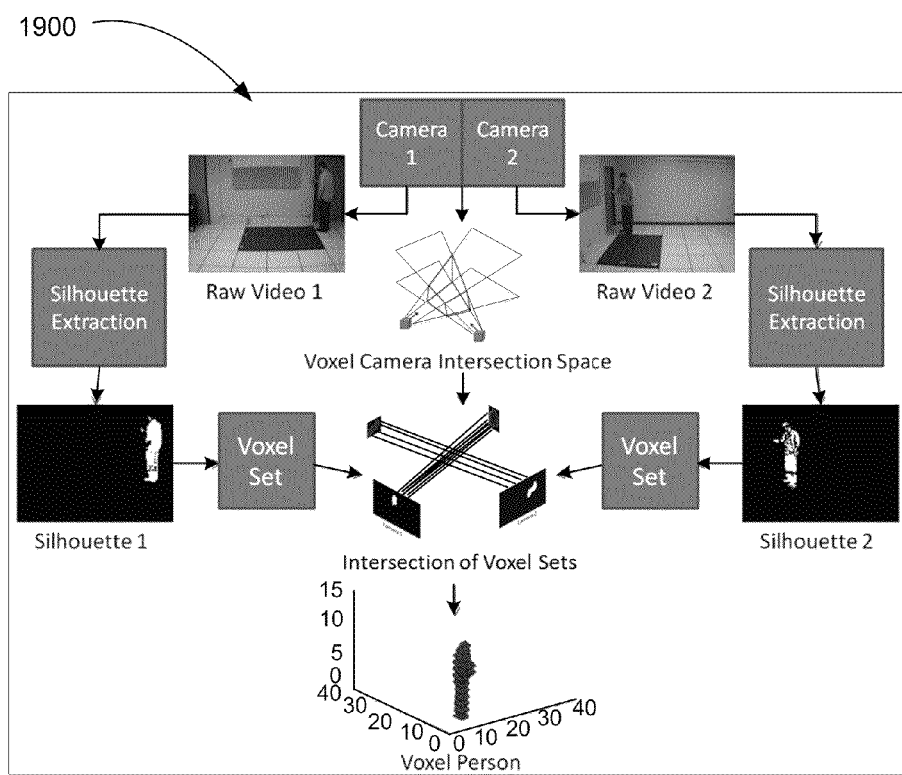

FIG. 19 illustrates a diagram of a voxel person construction 1900, according to an example embodiment. As shown in the voxel person construction 1900, the video cameras 206, 208 capture the raw video from different viewpoints, silhouette extraction is performed for each camera 206, 208, voxel sets are constructed from the silhouettes for each camera 206, 208, and the voxel sets are intersected to compute a voxel person. Camera positions may be recorded and intrinsic and rotation parameters may be estimated. For each pixel in the image plane, a set of voxels that its viewing ray intersects may be identified.

In some embodiments, voxel person construction may then just be an indexing procedure. There recalculate of the voxel-pixel intersections while building voxel person from the silhouettes may not need to be performed. The voxel-pixel test may, in some embodiments, be a procedure that is only computed one time when the video cameras 206, 208 are positioned in the room.

In some embodiments, an octree or binary spatial partition tree, can be used to speed up voxel-pixel set construction. In some embodiments, voxels belonging to the object can be further subdivided and tested on the fly for increased object resolution.

Figure 20:
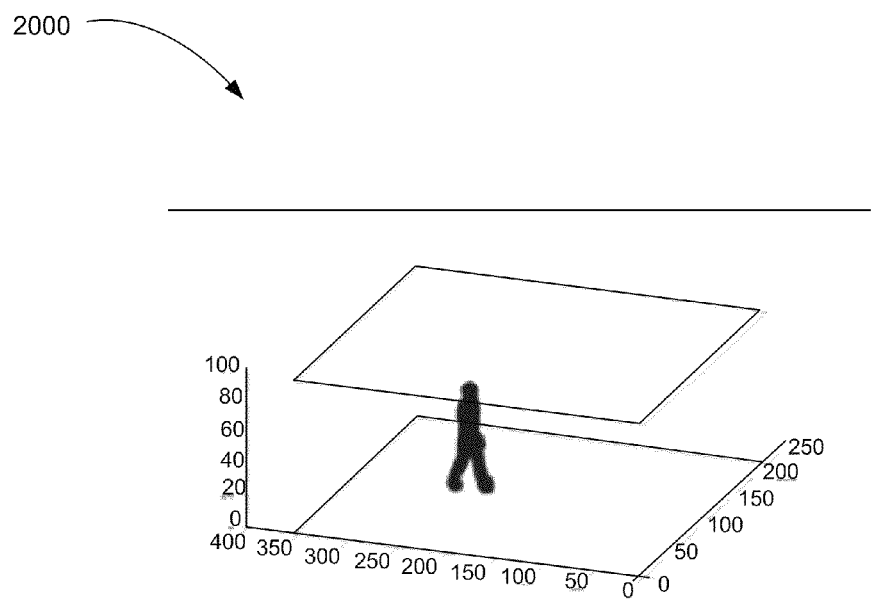

FIG. 20 illustrates a diagram 2000 of a voxel person in a three dimensional space, according to an example embodiment. As shown the voxel person is shown to have a certain volume and generally reflects the appearance of a person.

Figure 21:
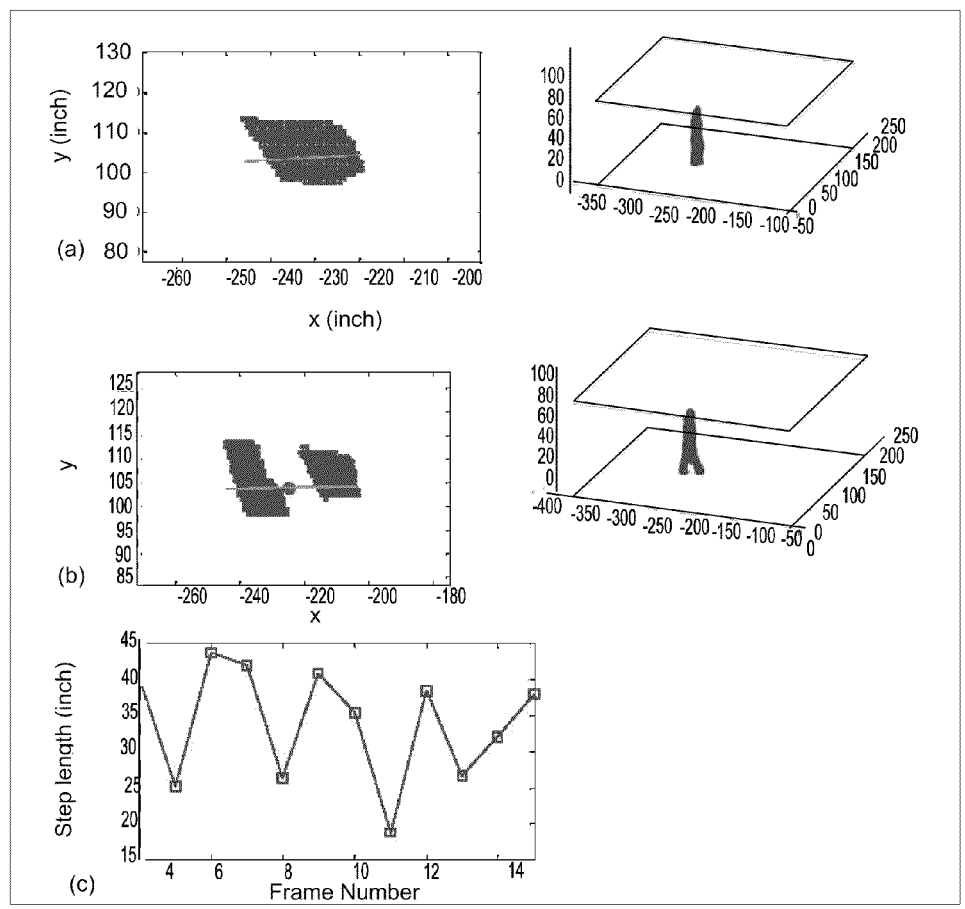

FIG. 21 illustrates a diagram 2100 of example projections, according to an example embodiment. The projections show a projection of a family frame or when the feet of the person are together, a projection of a peek frame or when the feet of the person are apart, and step length variation at different frames.

Figure 22:
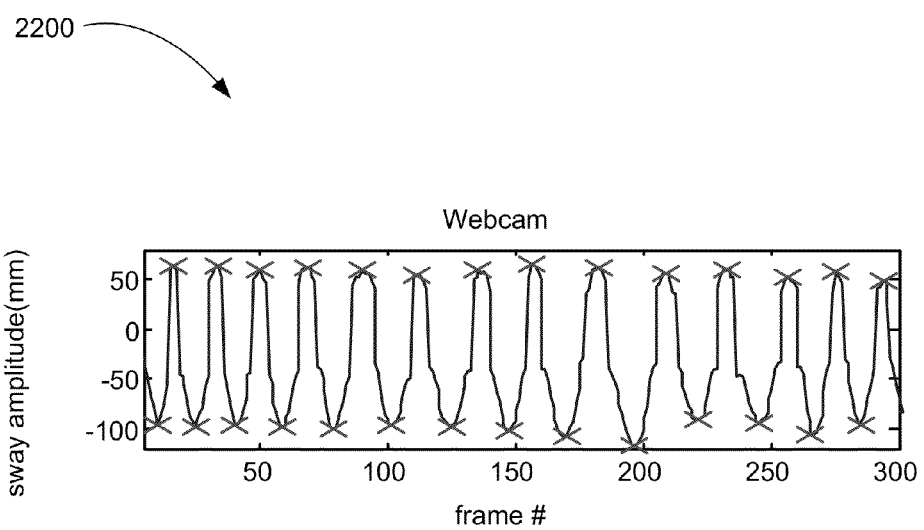

FIG. 22 illustrates a diagram 2200 of sample sway amplitude during standing, according to an example embodiment. Cross may mark the maximum sway amplitude and time (frame).

Figure 23:
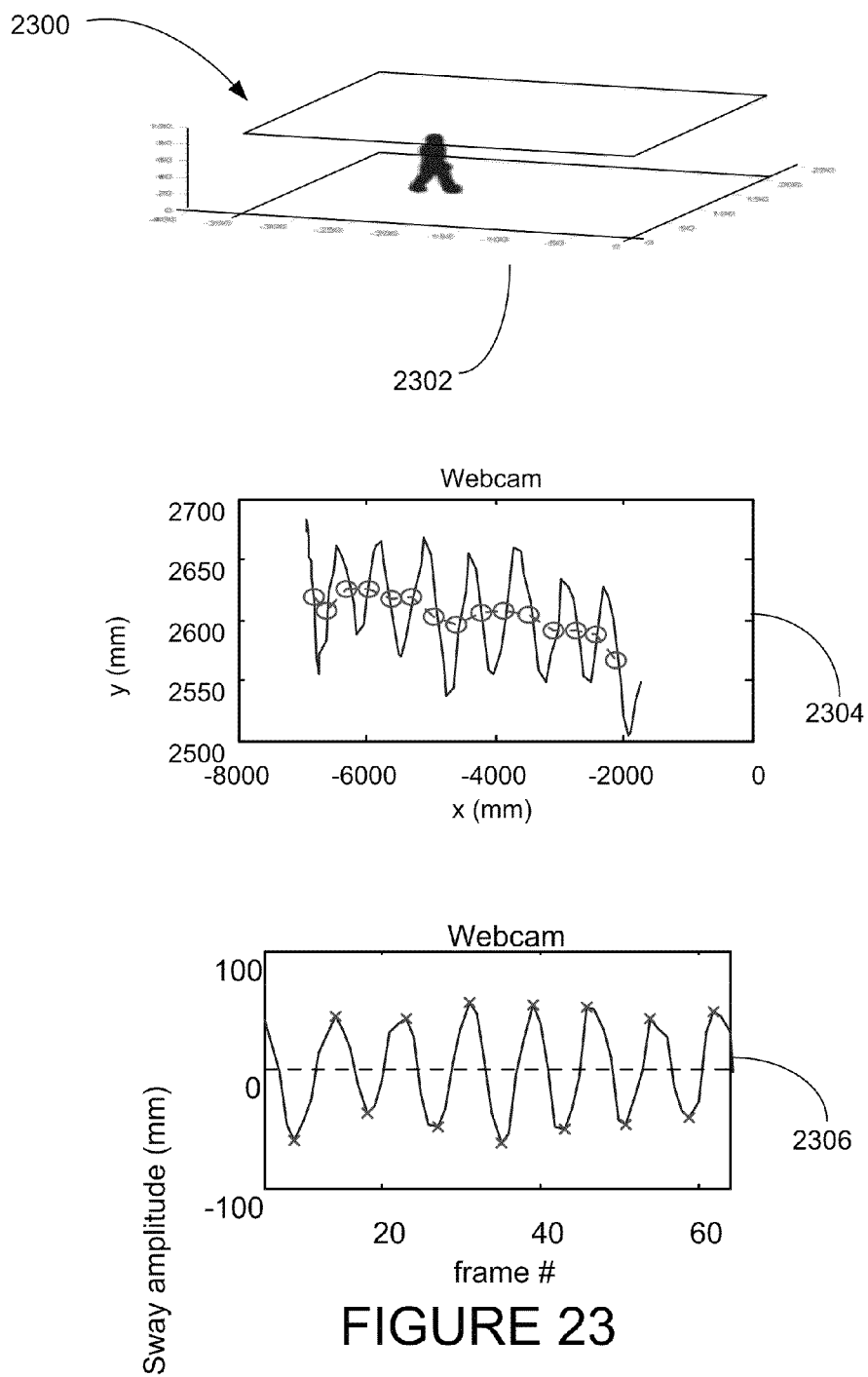

FIG. 23 illustrates a diagram 2300 associated with sway. A display 2302 is a sample voxel pursing during a walk, and displays 2304, 2306 illustrate the 2-D body centroid trajectory and extract sway amplitude during the sample walk.

After obtaining the silhouettes from the image sequence, extracting image moments may be extracted as shown in the diagram 2300. The image moments are applicable in a wide range of applications such as pattern recognition and image encoding. As shown, the steps for extracting image moments may include extracting images, performing pre-processing and silhouette extraction, extracting image moments, performing fuzzy clustering of the moments, and finding the nearest prototype matching and identifying sit and upright frames and/or using membership values to segment transition frames.

Figure 24:
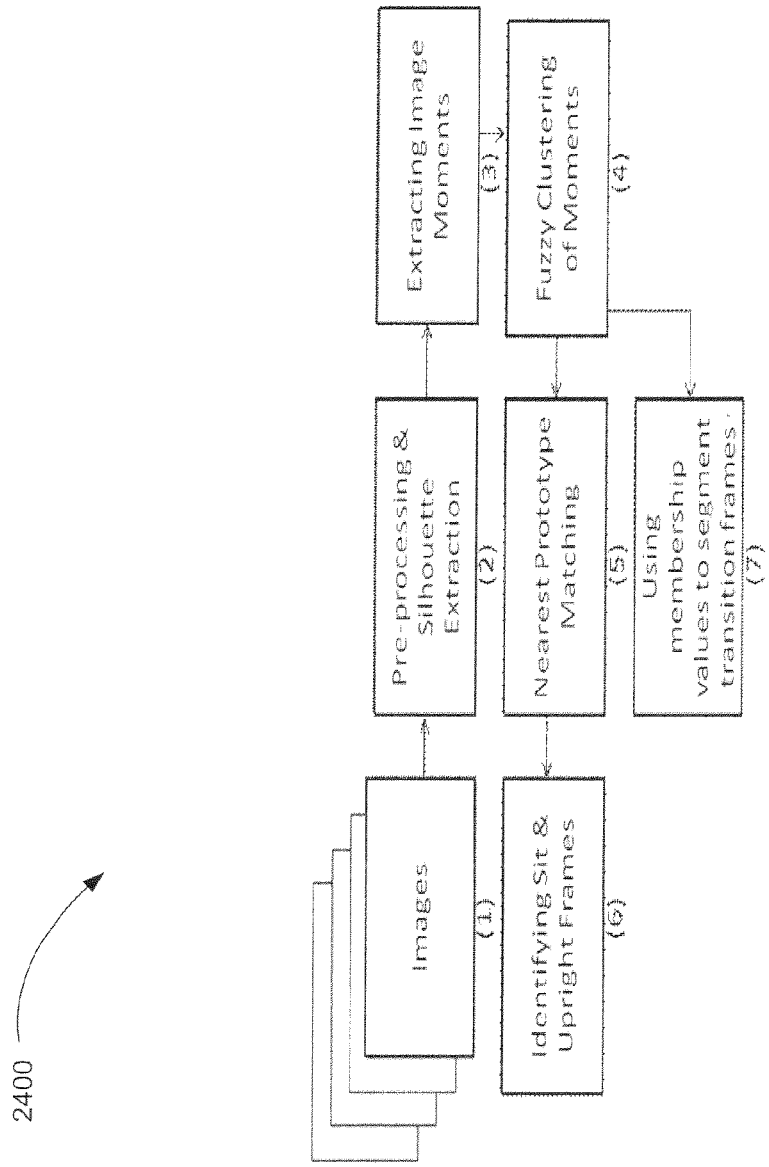

FIG. 24 illustrates a diagram 2400 for extracting image moments, according to an example embodiment. In some embodiments, the diagram 2400 is associated with the method 1500 (see FIG. 15).

Figure 25:
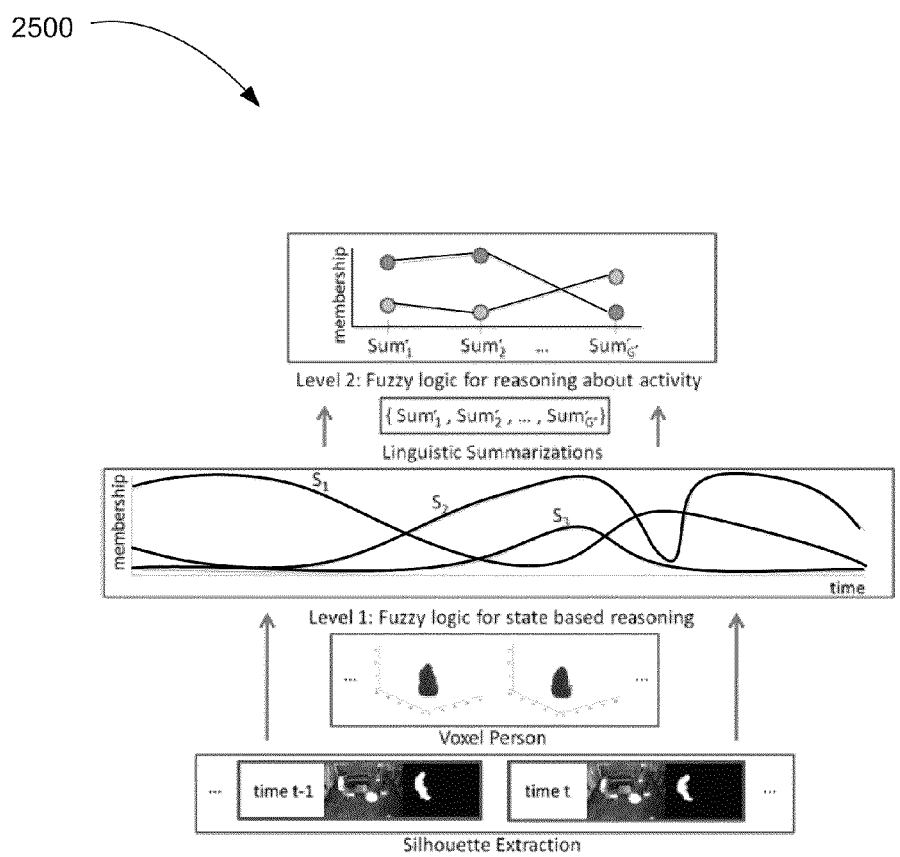

FIG. 25 illustrates a diagram 2500 for an activity recognition framework, according to an example embodiment. The activity recognition framework shown in the diagram 2500 may utilize a hierarchy of fuzzy logic based on a voxel person representation. The first level may include reasoning about the state of the individual. Linguistic summarizations may be produced and fuzzy logic may be used again to reason about human activity.

Figure 26:
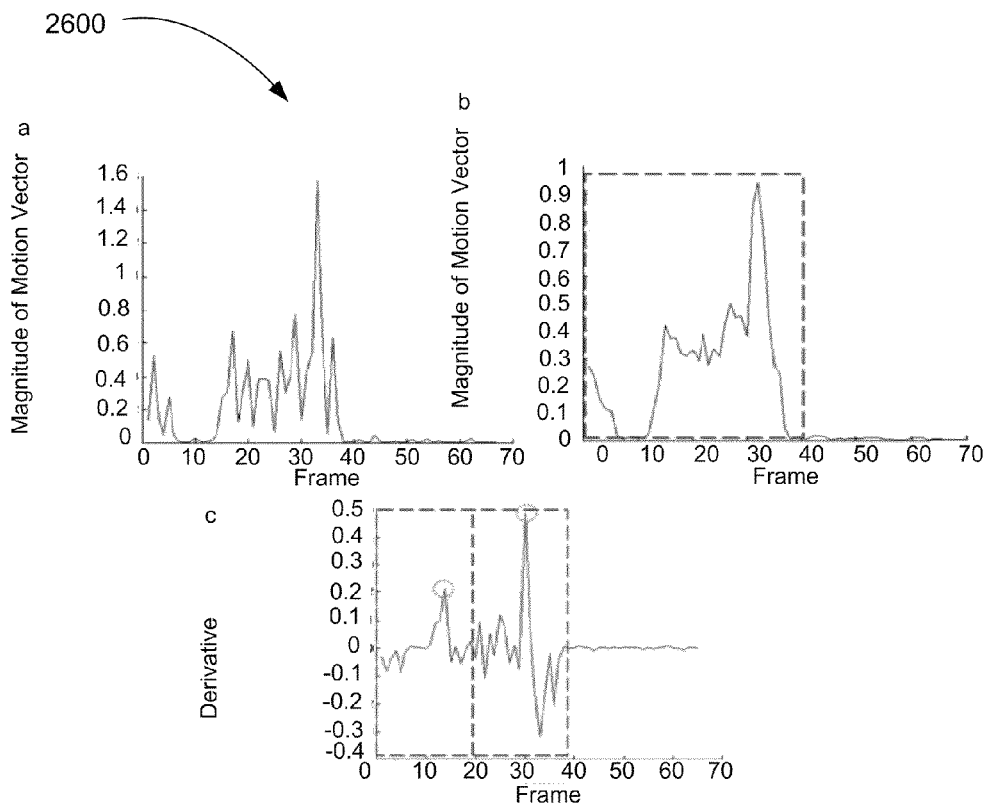

FIG. 26 illustrates a diagram 2600 for detection of a large recent change in voxel person's speed, according to an example embodiment. The diagram 2600 includes a diagrams showing (a) computation of motion vector magnitudes, (b) a fixed size window, placed directly before the start of the summarization, smoothed with a mean filter, and (c) the maximum of the derivative of the filtered motion vector magnitudes is found in the first and second halves of the window. The feature as shown is the ratio of the two maximum values.

FIG. 27 illustrates a diagram 2700 of an example table including fuzzy rules for activity analysis, according to an example embodiment.

Figure 28:
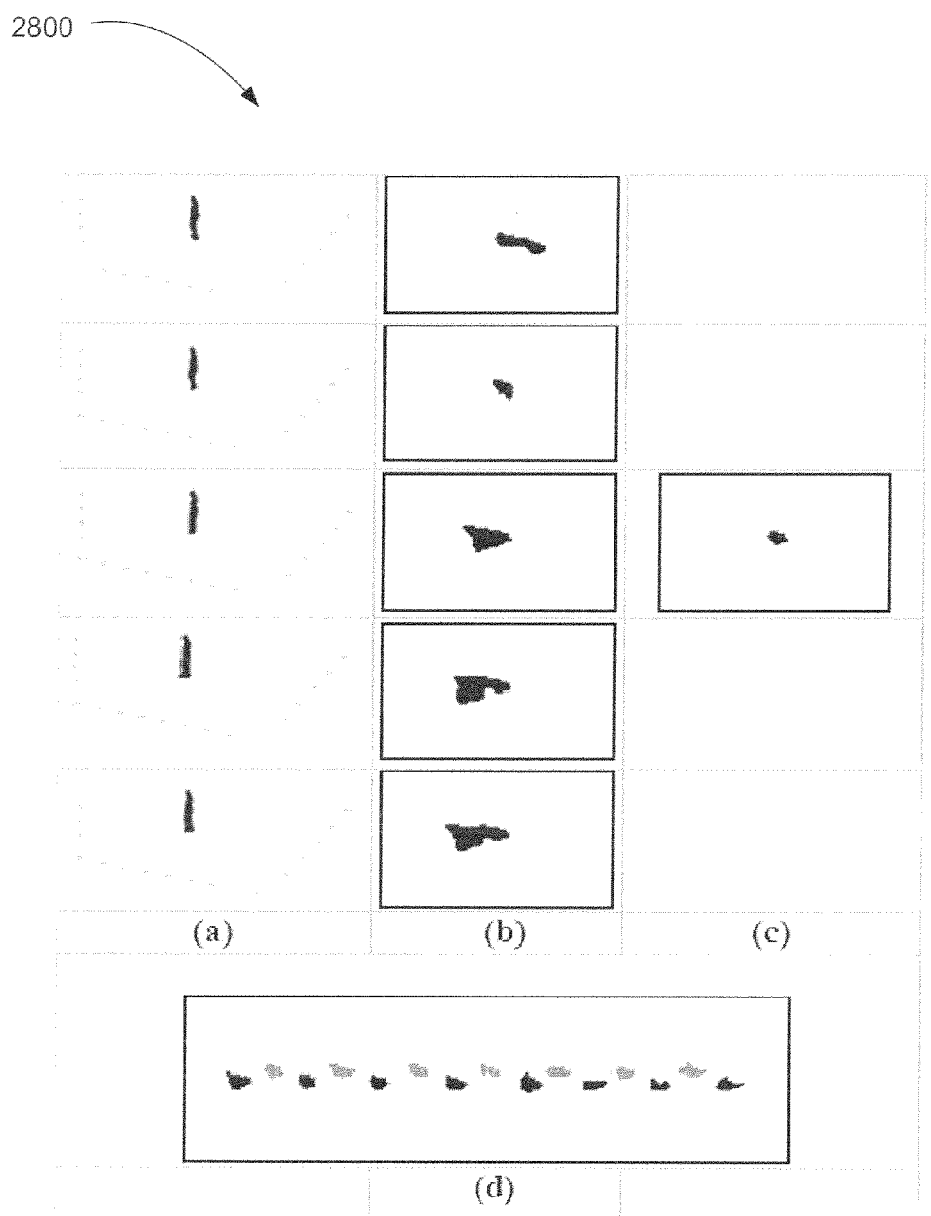

FIG. 28 illustrates a diagram 2800 of example frames, projections, and intersections associated with footsteps, according to an example embodiment.

Section (a) of the diagram 2800 shows the three dimensional voxel person model for five consecutive frames. Section (b) of the diagram 2800 shows ground plane projection of voxels below two inches for the frames. Section (c) of the diagram 2800 shows the intersection of projections for the frames. Section (d) includes points believed to belong to footfalls for entire frame sequence, with right/left classification of each footfall capable of indication by colors (e.g., green/blue respectively).

Figure 29:
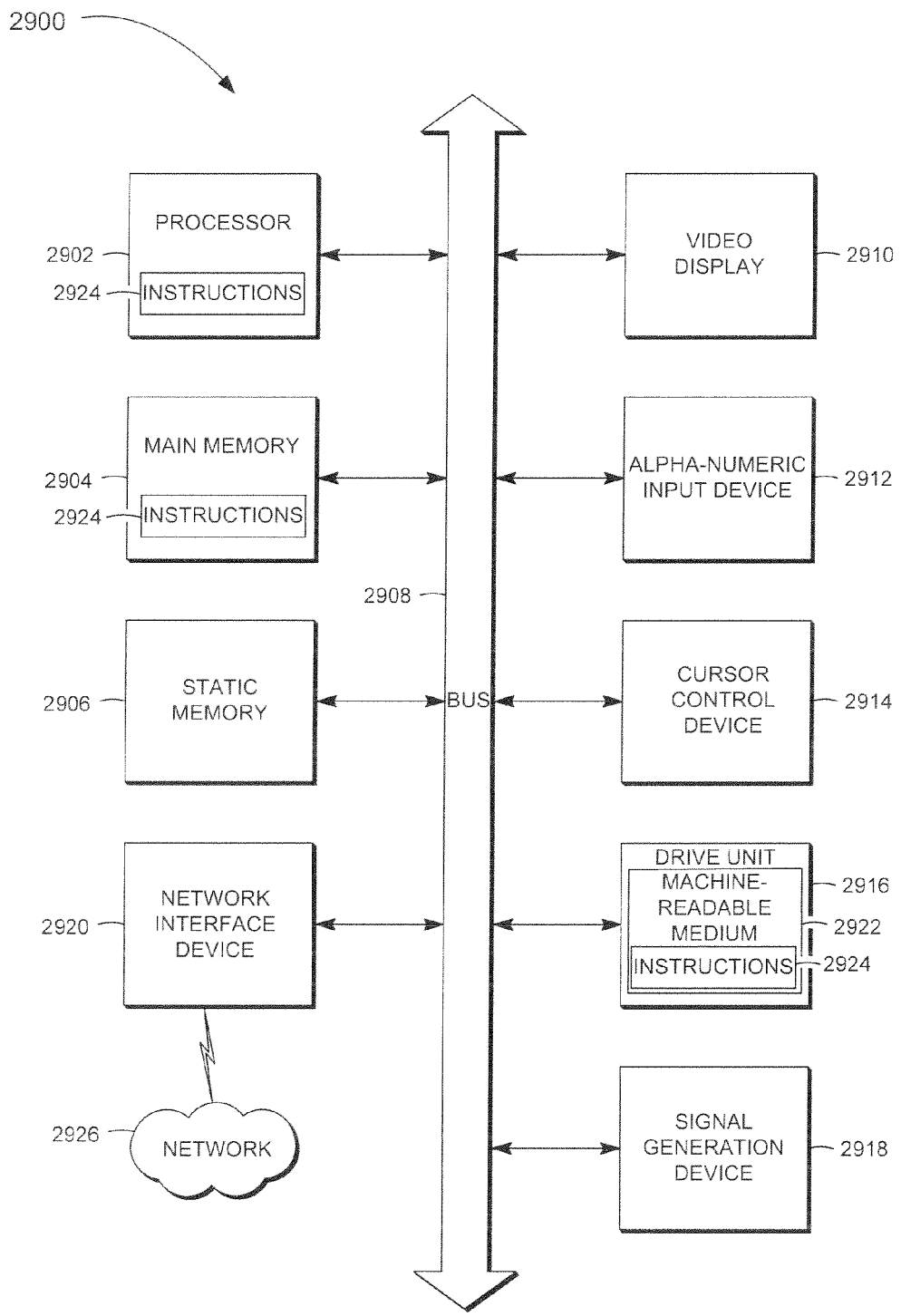
FIG. 29 is a block diagram of a machine in the example form of a computer system within which a set of instructions for causing the machine to perform any one or more of the methodologies discussed herein may be executed.

FIG. 29 shows a block diagram of a machine in the example form of a computer system 2900 within which a set of instructions may be executed causing the machine to perform any one or more of the methods, processes, operations, or methodologies discussed herein. The operator device 102, the provider device 106, or both may include the functionality of the one or more computer systems 2900.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a web appliance, a network router, switch or bridge, a kiosk, a point of sale (POS) device, a cash register, an Automated Teller Machine (ATM), or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 2900 includes a processor 2912 (e.g., a central processing unit (CPU) a graphics processing unit (GPU) or both), a main memory 2904 and a static memory 2906, which communicate with each other via a bus 2908. The computer system 2900 may further include a video display unit 2910 (e.g., a liquid crystal display (LCD) or a cathode ray tube (CRT)). The computer system 2900 also includes an alphanumeric input device 2912 (e.g., a keyboard), a cursor control device 2914 (e.g., a mouse), a drive unit 2916, a signal generation device 2918 (e.g., a speaker) and a network interface device 2920.

The drive unit 2916 includes a machine-readable medium 2922 on which is stored one or more sets of instructions (e.g., software 2924) embodying any one or more of the methodologies or functions described herein. The software 2924 may also reside, completely or at least partially, within the main memory 2904 and/or within the processor 2912 during execution thereof by the computer system 2900, the main memory 2904 and the processor 2912 also constituting machine-readable media.

The software 2924 may further be transmitted or received over a network 2926 via the network interface device 2920.

While the machine-readable medium 2922 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing or encoding a set of instructions for execution by the machine and that cause the machine to perform any one or more of the methodologies of the present invention. The term "machine-readable medium" shall accordingly be taken to include, but not be limited to, solid-state memories, and optical media, and magnetic media. In some embodiments, the machine-readable medium is a non-transitory machine readable medium.

Certain systems, apparatus, applications or processes are described herein as including a number of modules. A module may be a unit of distinct functionality that may be presented in software, hardware, or combinations thereof. When the functionality of a module is performed in any part through software, the module includes a machine-readable medium. The modules may be regarded as being communicatively coupled.

In an example embodiment, a first silhouette image of a person in a living unit may be accessed. The first silhouette image may be based on a first video signal recorded by the first video camera. A second silhouette image of the person in the living unit may be accessed. The second silhouette image may be of a different view of the person than the first silhouette image. The second silhouette image may be based on a second video signal recorded by a second video camera. The second video camera may be a different video camera than the first video camera. The first video camera and the second video camera may be positioned to record an area of the living unit from a different position in the living unit. A three-dimensional model of the person in voxel space may be generated based on the first silhouette image, the second silhouette image, and viewing conditions of the first video camera and the second video camera.

In an example embodiment, a plurality of three-dimensional models of a person in voxel space may be generated. The plurality of three-dimensional models may be associated with a time period. A particular three dimensional model may be based on a first silhouette image of a person in a living unit. The first silhouette image may be based on a first video signal recorded by a first video camera, a second silhouette image of the person in the living unit, and viewing conditions of the first video camera and the second video camera. The second silhouette image may be based on a second video signal recorded by a second video camera. The second video camera may be a different video camera than the first video camera. The first video camera and the second video camera may be positioned to record an area of the living unit from a different position in the living unit. The plurality of three-dimensional models may be analyzed to identify a first state and a second state of the person during the time period. A description may be selected based on analysis of the plurality of three-dimensional models. A display may be generated including the description.

Thus, methods and systems for anonymized video analysis have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

Various activities described with respect to the methods identified herein can be executed in serial or parallel fashion. Although "End" blocks are shown in the flowcharts, the methods may be performed continuously.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:

accessing a first silhouette image of a person in a living unit, the first silhouette image based on a first video signal recorded by a first video camera;

accessing a second silhouette image of the person in the living unit, the second silhouette image being of a different view of the person than the first silhouette image, the second silhouette image based on a second video signal recorded by a second video camera, the second video camera being a different video camera than the first video camera, the first video camera and the second video camera being positioned to record an area of the living unit from a different position in the living unit;

generating a three-dimensional model of the person in voxel space based on the first silhouette image, the second silhouette image, and viewing conditions of the first video camera and the second video camera;

accessing a third silhouette image of the person in the living unit, the third silhouette image based on the first video signal recorded by the first video camera, the third silhouette image associated with a different frame of the first video signal than the first silhouette image;

accessing a fourth silhouette image of the person in the living unit, the fourth silhouette image based on the second video signal recorded by the second video camera, the fourth silhouette image associated with a different frame of the second video signal than the second silhouette image;

analyzing a projection of a bottom section of the three-dimensional model of the person onto a ground plane of the living unit during the time period;

identifying a plurality of voxel intersections during a time period, a particular voxel intersection including an overlapping portion of the bottom section of the three-dimensional model of the person onto the ground plane on multiple frames, the third silhouette image being after the first silhouette image, the fourth silhouette image being after the second silhouette image;

calculating a voxel volume of the three-dimensional model of the person;

applying fuzzy set theory to the voxel volume of the three-dimensional model of the person based on an expected voxel volume of the person; and generating a fuzzified version of the three-dimensional model of the person in the voxel space based on the first silhouette image, the second silhouette image, the viewing conditions of the first video camera and the second video camera, and application of fuzzy set theory.

2. The method of claim 1, further comprising:
extracting a plurality of features from the three-dimensional model of the person.

3. The method of claim 2, further comprising:
applying fuzzy logic to extraction of the plurality of features to identify a state of the person.

4. The method of claim 2, wherein the plurality of features include an eigen height of the three-dimensional model of the person, a centroid of the three-dimensional model of the person, and a ground plane normal similarity of the three-dimensional model of the person.

5. The method of claim 4, further comprising:
extracting a plurality of features from the three-dimensional model of the person based on the first silhouette image and the second silhouette image;
applying fuzzy logic to extraction of the plurality of features from the three-dimensional model of the person to identify a first state of the person;
extracting a plurality of features from an additional three-dimensional model of the person based on a third silhouette image of the person in the living unit and a fourth silhouette image of the person in the living unit, the third silhouette image associated with a different frame of the first video signal than the first silhouette image, the fourth silhouette image based on the second video signal recorded by the second video camera, the fourth silhouette image associated with a different frame of the second video signal than the second silhouette image;
extracting the plurality of features from the additional three-dimensional model of the person based on the third silhouette image and the fourth silhouette image;
applying the fuzzy logic to the extraction of the plurality of features from the additional three-dimensional model of the person to identify a second state of the person; and
identifying an activity of the person as a falling activity when the three-dimensional model of the person transitions from an upright state to an on-the-ground state between the first state and the second state and includes a certain transition from the three-dimensional model of the person to the additional three-dimensional model of the person for at least some of the plurality of features.

6. The method of claim 1, further comprising:
analyzing a centroid of the three-dimensional model of the person during the time period, the centroid being a particular feature of the plurality of features; and
calculating a speed of the person during the time period based on the analysis of the centroid.

7. The method of claim 1, further comprising:
analyzing a projection of a bottom section of the three-dimensional model of the person onto a ground plane of the living unit during the time period; and
calculating step length and step time during the time period based on the analysis of the projection.

8. The method of claim 1, further comprising:
forming a plurality of spatial clusters based on identification of the plurality of voxel intersections to identify a plurality of footsteps, a particular footstep of the plurality of footsteps associated with a particular spatial cluster of the plurality of spatial clusters.

9. The method of claim 8, further comprising:
determining a direction of motion of the three-dimensional model of the person based on the plurality of footsteps.

10. The method of claim 8, further comprising:
identifying a left footstep, a right footstep, a left step length, a right step length, a left step time, a right step time, and shuffling based on the plurality of footsteps.

11. The method of claim 1, further comprising:
accessing a centroid of the three-dimensional model of the person, the centroid being a particular feature of the plurality of features;
computing a trajectory of the three-dimensional model of the person over the time period;
generating a varying angle and an amplitude of the three-dimensional model of the person based on the certroid and computation of the trajectory; and
identifying lateral sway of the three-dimensional model of the person based on generation of the varying angle and the amplitude.

12. The method of claim 2, further comprising:
accessing a centroid of the three-dimensional model of the person;
determining a base of support of the three-dimensional model of the person;
generating a varying angle and an amplitude of the three-dimensional model of the person based on the certroid and the base of the support; and
identifying body sway of the three-dimensional model of the person based on generation of the varying angle and the amplitude.

13. The method of claim 1, further comprising:
extracting a first feature from the first silhouette image and the second silhouette image;
extracting a second feature from the three-dimensional model of the person; and
identifying sit to stand time based on extraction of the first feature and the second feature.

14. The method of claim 1, further comprising:
receiving a first video signal from a first video camera, the first video signal including a depiction of the person;
receiving a second video signal from a second video camera, the second video signal including a different depiction of the person, the different depiction of the person being of the person from a different view than the depiction of the person;
generating the first silhouette image of the person from the first video signal; and
generating the second silhouette image of the person from the second video signal.

15. The method of claim 1, further comprising:
generating a display of the three-dimensional model of the person, the display including a silhouetted depiction of the three-dimensional model in the living unit.

16. The method of claim 1, wherein the first video camera and the second video camera are approximately 90 degrees apart from each other in the living unit in reference to the person.

17. The method of claim 1, wherein the first silhouette image and the second silhouette image are associated with the person being in a same position in the living unit.

18. The method of claim 1, wherein the first silhouette image and the second silhouette image are associated with a similar moment in time.

19. The method of claim 1, wherein the viewing conditions include a location of the first video camera and the second video camera in the living unit, orientation of the first video camera and the second video camera, and a lensing effect of the first video camera and the second video camera.

20. The method of claim 1, further comprising:
using the three-dimensional model of the person in voxel space to monitor wellbeing of the person in the living unit.

* * * * *